(12) United States Patent
Lv et al.

(10) Patent No.: US 8,097,586 B2
(45) Date of Patent: Jan. 17, 2012

(54) MODIFIED EXEDINS AND USES THEREOF

(75) Inventors: Aifeng Lv, Jiangsu (CN); Changan Sun, Jiangsu (CN); Yali Wang, Jiangsu (CN)

(73) Assignee: Wuxi Grandchamp Pharmaceutical Technology Co., Ltd., Jiangsu (CN)

( * ) Notice: Subject to any disclaimer, the term of this patent is extended or adjusted under 35 U.S.C. 154(b) by 561 days.

(21) Appl. No.: 11/813,917

(22) PCT Filed: Jan. 10, 2006

(86) PCT No.: PCT/CN2006/000029
§ 371 (c)(1),
(2), (4) Date: Jul. 13, 2007

(87) PCT Pub. No.: WO2006/074600
PCT Pub. Date: Jul. 20, 2006

(65) Prior Publication Data
US 2010/0009904 A1    Jan. 14, 2010

(30) Foreign Application Priority Data
Jan. 14, 2005   (CN) .......................... 2005 1 0038102

(51) Int. Cl.
*A61K 38/00*     (2006.01)
*A23J 1/00*      (2006.01)

(52) U.S. Cl. ............ 514/7.2; 514/3.2; 514/6.7; 514/6.9; 514/7.3; 530/412; 530/421

(58) Field of Classification Search .................. None
See application file for complete search history.

(56) References Cited

U.S. PATENT DOCUMENTS

| 6,767,887 B1 * | 7/2004 | Hoffmann et al. ................ 514/2 |
| 6,969,702 B2 * | 11/2005 | Bertilsson et al. .............. 514/12 |
| 2004/0029784 A1 * | 2/2004 | Hathaway ......................... 514/8 |

FOREIGN PATENT DOCUMENTS

| WO | WO 00/66629 | * | 4/2000 |
| WO | 0066629 A1 | | 11/2000 |
| WO | 0104156 A1 | | 1/2001 |
| WO | 2004022004 A3 | | 3/2004 |

OTHER PUBLICATIONS

Tsubery H et al.; "Prolonging the Action of Protein and Peptide Drugs by a Novel Approach of Reversible Polyethylene Glycol Modification"; J. Biol. Chem, vol. 279, No. 37, Sep. 10, 2004, pp. 38118-38124.

Eng J et al.; "Isolation and Characterization of Exendin-4, an Exendin-3 Analogue, from *Heloderma suspectum* Venom", J. Biol. Chem, vol. 267, No. 11, Apr. 15, 1992, pp. 7402-7405.

Michael A N et al.; "Glucagon-like peptide 1 and its derivatives in the treatment of diabetes"; Regulatory Peptides, vol. 128, Sep. 8, 2004, pp. 135-148.

\* cited by examiner

*Primary Examiner* — Robert Landsman
*Assistant Examiner* — Ian Dang
(74) *Attorney, Agent, or Firm* — Norris McLaughlin & Marcus, P.A.

(57) ABSTRACT

Novel exendins with modifications at one or more of following positions: 2, 14, 27 or 28 and polyethylene glycol derivatives thereof are provided. These compounds are useful in treating type 2 diabetes as GLP-1 receptor agonists.

13 Claims, 4 Drawing Sheets

MODIFIED EXEDINS AND USES THEREOF

FIELD OF THE INVENTION

The present invention relates to long-lasting exendins and pharmaceutical acceptable salts thereof. To be more particular, the present invention relates to pegylated exendins and pharmaceutical acceptable salts thereof, and preparation method thereof as well as their uses in preventing and treating type 2 diabetes by regulating the blood glucose level due to the stimulation of the secretion of insulin from β-cell induced by the Glucagon-like peptide 1 (GLP-1) receptor acting with said compounds.

BACKGROUND ART

Recently, accompanying with the increased living standard, modernization of living style and aging of society, incidence of diabetes is also kept increasing on a yearly basic all over the world, of which the situation is especially obvious in developing countries. Diabetes has become the third major chronic non-communicable disease next to malignant tumors, cardio-cerebrovascular diseases, and constituted the major causes to death and disability. As reported in WHO report of 1997 that by that time there are 135 millions of people suffering from diabetes and 175 millions are expected to be reached by 2000. In China, a recent report shows that incidence of diabetes in the population of age over 20 is 3.21%. A preliminary estimation shows that there are at least 20 millions of diabetes patients in China nowadays, in which over 95% of them are type 2 diabetes patients. From 1987 to 1992, the annual outlay for direct or indirect uses in diabetes in United State increased from 1 billion to 92 billion US Dollars. In China, the outlay for treatment of diabetes is also increasing at an incredible speed. According to a related statistical analysis reported in 1993 that up to 2.2 billions dollars were spend on the treatment of diabetes at that time, in which neither the cost for the treatment of diabetes complications, outlay for out-hospital treatments and health care nor indirect loss in social economy were included.

Type 2 diabetes can be controlled by moderation of dietary intake, exercise and regulation of the blood-glucose level with medication. Commonly employed medication includes insulin, sulphonylurea, biguanide as well as Glitazone compounds. These compounds help only in promoting the blood-glucose level back to the normal level while unable to recover the impairments, especially to kidney, cardiovascular system, optical or nervous system caused by diabetes complications. These complications are closely associated with the increased mortality caused by diabetes. The major side effects inherent in the first generation of diabetic medications include low in blood-glucose level, increase in body-weight and dropsy. The acting mechanisms of these medications maybe different, however, none of them is able to protect the insulin-secreting β-cell, thereby, the in vivo blood glucose metabolism and incretion regulation cannot be maintained in normal condition. In most cases, consecutive use of a single medicine renders it no longer effective, which gives rise to the application of combined drug treatment. Since diabetes patients take blood pressure-lowering and cholesterol reducing drugs simultaneously during treatment, the long-term effect of this treatment is not stable. Therefore, development of new medications to cooperate with current medications for the regulation of blood glucose level, and to achieve the objects in protecting and recovering the functionality of β-cell as well as adjusting incretion in response to food intake would result in a great improvement in diabetic treatment.

Investigation of Glucagon-like peptide-1 (GLP-1) receptor agonist is a likely topic. Investigation and development in this field may open a new chapter in the treatment of type 2 diabetes. Glucagon-like peptide-1 was firstly discovered in 1984, which is a kind of intestinal secretion hormones. If type 2 diabetics were injected with this hormone, their blood glucose level can be adjusted to a normal level (Nathan, D M, et al. Diabetes Care 1992; 15:270-6; Zander, M, et al. Lancet 2002; 359:824-30). It was reported that action of Glucagon-like peptide and receptor agonist thereof is mainly caused by insulin secretion induced by activating the Glucagon-like peptide 1 receptor on the surface of the pancreas β-cell. Since this effect depends on the in vivo blood glucose level, fatal hypoglycemic shock caused by the extremely low blood glucose level even in the presence of Glucagon-like peptide and receptor agonist thereof would not occur like the traditional medication does. More particularly, when the in vivo blood glucose level is higher than 6 mmol/L, GLP-1 remarkably stimulates secretion of insulin, whereas when the in vivo blood glucose level reaches the normal level, the stimulation discontinue. Also, this type of agonist stimulates the proliferation of pancreas β-cell of rodent (rat) and also enhances the action of β-cell tissue. The function that allows the recovery of the pancreas β-cell opens up prospects for the treatment of type 2 diabetes by at least delaying the onset of type 1 diabetes from type 2 diabetes. Meanwhile the Glucagon-like peptide and receptor agonist thereof is able to inhibit the secretion of glucagon, and thereby make it possible to reduce the output of blood glucose from liver. More importantly, this type of agonist reduces the dietary intake by inhibiting the gastrointestinal peristalsis and gastric emptying, thereby reduces the body weight and also helps in controlling the body weight of type 2 diabetics.

DETAIL DESCRIPTION OF INVENTION

The objective of the present invention is to provide long-lasting pegylated exendins and pharmaceutical acceptable salts thereof. They can induce the secretion of insulin and decrease the blood glucose level by activating Glucagon-like peptide 1 (GLP-1) receptor and thereby useful in treating and preventing type 2 diabetes. This type of compounds have a long retention time in vivo and exhibits a prolonged action therein. The prolonged retention is not only due to the delay of renal excretion caused by pegylation, but also due to the improved in vivo enzymatic and chemical stability of the peptide backbone resulted from the pegylation. Pegylation ensures the long-lasting effect of these compounds and thereby reduces the injection times to patients, and patients may get the benefits of improved quality and effectiveness of such therapy.

More particularly, the present invention relates to, but is not limited to all pegylated polypeptide precursors listed in the sequence table, and compounds modified with polyethylene glycol with various molecular weights, and pharmaceutical acceptable salts thereof.

Another objective of the present invention is to provide a method for the preparation of long-lasting pegylated exendins and pharmaceutical acceptable salts thereof.

Still another objective of the present invention is to provide the use of the long-lasting exendins and/or pharmaceutical acceptable salts thereof as a Glucagon-like peptide 1 (GLP-1) receptor agonist in treating and preventing type 2 diabetes.

The following technical solutions achieve the objectives of the present invention. The present invention relates to exendins and pharmaceutical acceptable salts thereof whose peptide backbone possesses optimized in vivo enzymatic and chemical stability. Particularly, the present invention relates to exendins comprising (A) amino acid sequences of SEQ ID Nos 4 to 141, (B) amino acid sequences substantially identical to those of SEQ ID Nos. 4 to 141.

The present invention also relates to exendins and pharmaceutical acceptable salts thereof derived from single or multiple pegylation at position 2, 14, 27, 28 of the exendins amino acid sequences of SEQ ID Nos. 4 to 141, in which molecular weight of said polyethylene glycol is within the range of 5,000 to 80,000, preferably 20,000 to 60,000. The amino acids of the exendins of the present invention possess critical sites for modification, which include position 2, 14, 27, 28 of the amino acid sequences of exendins.

Also, the objective of the present invention is to provide a method for the preparation of the above-mentioned exendins and pharmaceutical acceptable salts thereof, which includes solid-phase and solution-phase synthesis, purification by reverse-phase high performance liquid chromatography, ion-exchange and gel filtration, and lyophilization.

The present invention further provides the use of the exendins or pegylated exendins and pharmaceutical acceptable salts thereof in treating and/or preventing type 2 diabetes.

Clinic trails show that when type 2 diabetics, whose blood glucose level was poorly controlled, were subjected to Glucagon-like peptide 1 (GLP-1) treatment, their fasting blood glucose level become normal (Gutniak, et al., New Eng. J. Med. 326:1316-1322, 1992). Long term administration of Glucagon-like peptide 1 (GLP-1) can restore the functions of β-cell to normal level (Rachman, et al., Diabetes 45:1524-1530, 1996). Glucagon-like peptide 1 (GLP-1) can restore the glucose-response function of β-cell in those patients having functional imperfection of glucose tolerance (Byrne, et al., Diabetes 47:1259-1265, 1998). Since Glucagon-like peptide 1 (GLP-1) is readily inactivated by dipeptidyl peptidase (DPP IV) in vivo and many cleavage-points for other endopeptidase (NEP24.11) are present in the Glucagon-like peptide 1 (GLP-1), the in vivo lasting time of Glucagon-like peptide 1 (GLP-1) is short. Promising therapeutic effects of Glucagon-like peptide 1 can be achieved only by means of continuous administration. In this regard, researchers focus on the development of a more stable Glucagon-like peptide 1 (GLP-1) receptor agonist, mainly formed as modified Glucagon-like peptide 1 (GLP-1). More importantly, in the late 1980s and the early 1990s, Eng et al. isolated Exendin-4 from the saliva secretion organs of the Gila monster (Heloderma Sespectrum) in southwestern America (Eng, J. et al., J. Biol. Chem., 265:20259-62, 1990, Eng, J., et al. J. Biol. Chem., 267:7402-05, 1992). Exendin-4 is a polypeptide having 39 amino acids, which shows 53% homology with Glucagon-like peptide 1 (GLP-1). Exendin-4 shows affinity to GLP-1 receptor, and it possesses stronger ability than GLP-1. Its ability in adjusting glucose metabolism is better than GLP-1; its minimum concentration for the stimulation of insulin secretion is lower than GLP-1; and more importantly, the in vivo half-life of Exendin-4 is longer than that of GLP-1 (Kudsen, L. B. J. Med. Chem. 47:4128-4134, 2004). These are mainly due to the unique enzymatic stability of Exendin-4, which is originated from the elimination of the cleavage-sites of endopeptidase (such as NEP24.11).

Compounds which possess the function of Glucagon-like peptide 1 (GLP-1) receptor agonist, such as GLP-1 (7-36), GLP-1 (7-37), Exendin-4 and other derivatives of GLP-1 and Exendin-4, have been widely reported in many publications, which include WO98/43658, WO00/15224, WO00/66629, WO01/98331, WO01/04156, U.S. Pat. No. 5,545,618, U.S. Pat. No. 5,118, WO03/058203, U.S. patent application Ser. No. 60/395,738, WO04/022004 and their references cited therein.

Naturally existing GLP-1 receptor agonists are provided in the following table:

| Peptide | Sequence | SEQ ID NO |
|---|---|---|
| GLP-1 (7-36) | HAEGTFTSDV SSYLEGQAAK EFIAWLVKGR-NH2 | 1 |
| GLP-1 (7-37) | HAEGTFTSDV SSYLEGQAAK EFIAWLVKGRG | 2 |
| Exendin-4 | HGEGTFTSDL SKQMEEEAVR LFIEWLKNGG PSSGAPPPS-NH2 | 3 |

Abbreviation in the above sequences: H (His) histidine, A (Ala) alanine, E (Glu) glutamic acid, G (Gly) glycin, T (Thr) threonine, F (Phe) phenylalanine, S (Ser) serine, D (Asp) aspartic acid, V (Val) valine, Y (Tyr) tyrosine, L (Leu) leucine, Q (Gln) glutamine, K (Lys) lysine, I (Ile) isoleucine, R (Arg) arginine, M (Met) methionine, N (Asn) asparagine, P (Pro) proline.

Although more stable GLP-1 receptor agonists have been developed in many laboratories, their in vivo lasting time is still short, and thereby development of long-lasting derivatives of exendins acting as GLP-1 receptor agonists is in great demand. Since the window for the therapeutic effect and side effect (vomit and nausea) is relatively narrower, the use of sustained release formulation affords only a small chance of success. The only possible way to obtain a long-lasting GLP-1 receptor agonist is to prepare a stable compound having sufficiently long in vivo retention time.

Incorporation of polyethylene glycol into active protein or polypeptide increases the retention time of active protein and polypeptide. This technology has been successfully applied in many protein-based biological drugs, such as PEG-Intron, PEGASYS, Neulasta and Somavert and the like. The methods and chemistry for the incorporation of polyethylene glycol into protein and peptide backbone are provided in relevant references, such as the review by Veronese (Veronese, F M, Biomaterial 2001 22:405-417). In view of the fact that both GLP-1 and Exendin-4 belong to GLP-1 receptor, U.S. Pat. No. 5,424,286 and PCT WO98/05351 disclose the comparative experiments of GLP-1 and Exendin-4 in terms of their in vivo insulinotropic secretion function. The experiments showed that Exendin-4 exhibited a stronger and longer in vivo effect than GLP-1 due to its higher stability against the in vivo polypeptide hydrolase (DPP IV, NEP24.11 and the like). PCT WO2004/022004 discloses the pegylated GLP-1 receptor agonist, and proposes that when polyethylene glycol with molecular weight more than 30,000 daltons is employed, side effects, such as nausea and vomit, caused by the activation of the intracephalic GLP-1 receptor, are unlikely to occur with the resulting derivatives. It indicates that pegylated GLP-1 receptor agonist does not only prolong the in vivo acting time, but also minimize its side effects. However, this type of compounds show no improvement in the in vivo enzymatic and chemical stability of their polypeptide backbone in addition to the limitation in their in vivo or in vitro activity, which limits this type of compound acting as desired long-lasting therapeutic agent. The reduced in vivo and in vitro activity may increase the production cost of long-lasting therapeutic agent. In view of the above reasons, using Exendin-4 backbone as the precursor in pegylation may afford a greater chance of success in preparing long-lasting therapeutic agent, in which the polypeptide backbone possesses better enzymatic stability. Although PCT WO00/66629 discloses the resulting compounds and methods involving Exendin-4 as the precursor in pegylation, there is still a long way to go for a successful preparation of a long-lasting therapeutic agent with low production cost. It is because cleavage is likely to occur to His-Gly residue at the N-terminal by dipeptidyl peptidase (such as DPP IV), which renders the GLP-1 receptor agonist inactive no matter that Exendin-4 is able to prolong the in vivo retention time from a few hours to several dozen of hours, or even longer. Meanwhile, the long-lasting pegylated GLP-1 receptor agonist should have good chemical stability, especially at the in vivo temperature, i.e., 37° C., which is highly required for Exendin-4, of which the methionine residue at position 14 of Exendin-4 backbone is readily undergone oxidation giving rise to the mutation of its biological activity, by which preparation of therapeutic agent is made troublesome; and furthermore, hydrolysis of the asparagine residue at position 28 is the major cause for the inactivation of therapeutic agent as well as the preparation problem, the mechanism of hydrolysis is shown as below:

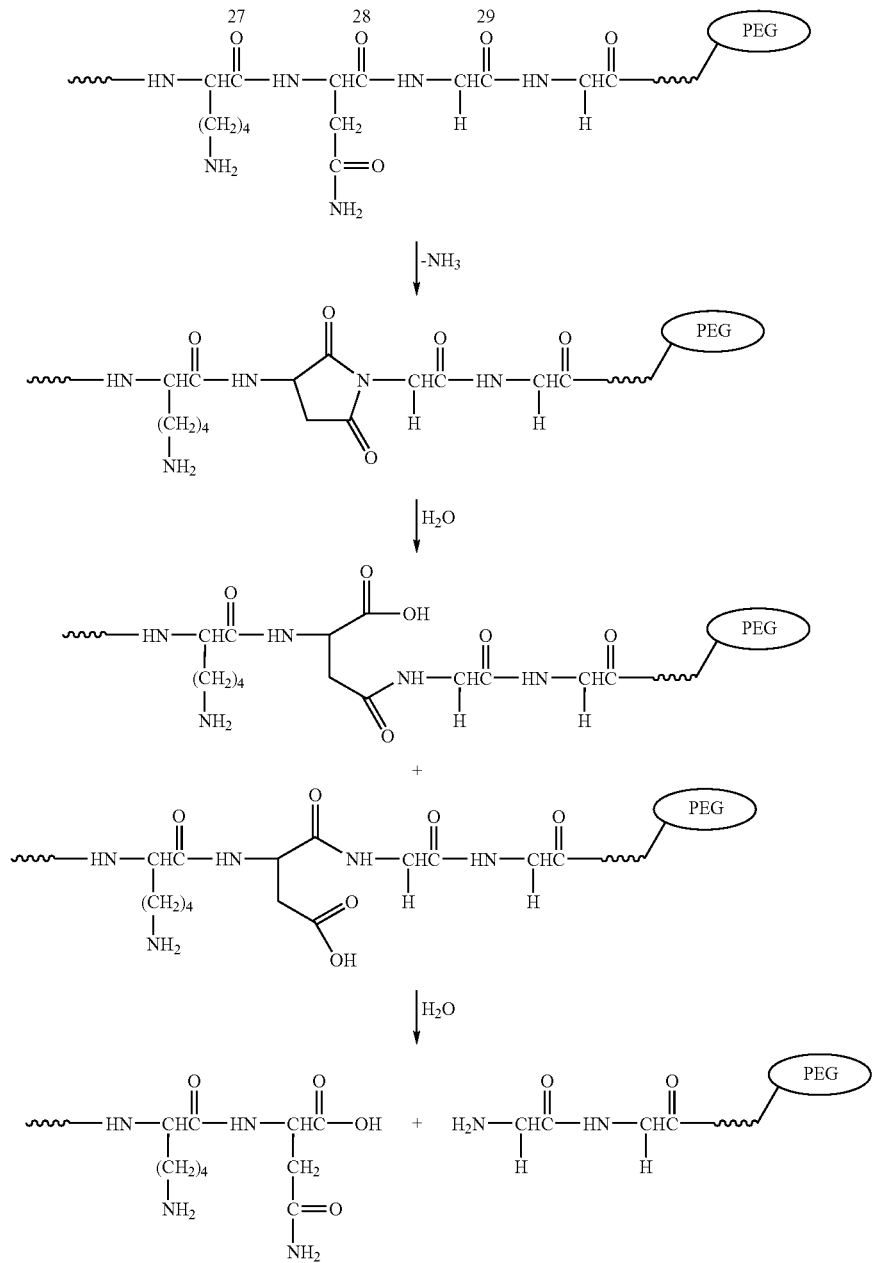

From the mechanism, it shows that hydrolysis of the five-membered ring derived from asparagine does not only decrease the activity of GLP-1 receptor agonist, but also cause to the separation of polyethylene glycol from the polypeptide backbone, and thereby adversely effect the in vivo retention time of the long-lasting compound. Accordingly, modification on glycine at position 2 enhances the enzymatic and chemical stability of the Exendin-4 polypeptide backbone; and modifications on methionine at position 14 and on asparagine at position 28 enhance the chemical stability of Exendin-4 polypeptide backbone as well. PCT WO00/66629 emphasizes on the preparation of polyethylene glycol conjugate via acylation with the amino group of the lysine side chain incorporated during pegylation of Exendin-4. Since Exendin-4 itself possesses lysine, selectivity of the acylation reaction is only achievable with suitable use of protecting groups, and thus renders the production cost higher. By locating the connection point between the polyethylene glycol for modification and the regiospecific group at the carboxyl terminal (C-terminal) of the polypeptide, action between the polypeptide and the receptor would not be affected by the polyethylene glycol, whereas a regiospecific reaction can be achieved, and thereby lowers the production cost.

The present invention discloses a series of derivatives of Exendin-4 pegylated at position 2, 14, 27, or 28, as well as the exendins obtained from pegylation conducted with these polypeptide backbones. These pegylated exendins exhibit long-lasting effect in vivo, which can be formulated as long-lasting therapeutic agent for injection use.

The exendins of the present invention allows the in vivo and in vitro activation of the GLP-1 receptor which locates on the surface of β-cell, which further allows the secretion of insulin and thereby lowers the blood glucose level. Examples of the exendins include, but not limited to, the polypeptide sequences in table 1 as well as those pegylated compounds. Serine at position 39, where pegylation takes place, can be substituted with cysteine or other mercapto-containing synthetic amino acid. Similarly, multiple pegylations can be achieved in the following way, in which two or more mercapto-containing amino acids (such as cysteine) are added to the carboxyl terminal, and the resulting elongated polypeptides derivatives may serve as the pegylation precursor. The general formula for the precursor of two-site modification is $Cys_{(39)}-(Xaa)_{n-1}-Cys_{(n+39)}$, wherein n=0-10, Xaa is any one of the amino acids.

The above-mentioned polypeptides can be prepared by chemical synthetic methods, which include liquid-phase synthesis of fragment, solid-phase synthesis (see Merrifield, J. Am. Chem. Soc. 1963, 85:2149-2154), or combined method of solid-phase and liquid-phase; polypeptide synthesis can be conducted manually or automatically. Applied Biosystems 431A polypeptide synthesizer, Csbio polypeptide synthesizer and the like can be employed in automatic synthesis; and also combinatorial synthesis can be used in polypeptide synthesis.

Purification by preparative HPLC is required for the polypeptides prepared by chemical synthetic method, reveres phase materials are commonly used as the column packing materials (such as $C_4$, or $C_8$, or $C_{18}$). In vivo and in vitro studies of the therapeutic effectiveness are only allowed after characterizations with analytical identifications (such as high performance liquid chromatography (HPLC), mass spectroscopy (MS), amino acids analysis (AAA)). After purification by preparative HPLC, products can be afford after lyophilization Polyethylene glycol can be purchased from a variety of suppliers or synthesized by common methods. Molecular weight of polyethylene glycol is usually within the range of 5,000-80,000 daltons, preferably 20,000-60,000 daltons and more preferably about 40,000 daltons.

Polyethylene glycol should be connected with polypeptide at the C-terminal of the polypeptide, so as to minimize the interferences caused by the polyethylene glycol to the action between polypeptide and the receptor. That is to say, polyethylene glycol may connect to any residues locating between positions 29 to 39, which involves substitutions of any one or any few of the amino acids with mercapto-containing amino acid (such as cysteine). In the case of single pegylation, it is better to substitute serine locating at position 39, carboxyl terminal with cysteine; similarly, in the case of two-site modification, the best way is to substitute serine at position 39 with cysteine and add another cysteine at position 40 or 39+n (n=1-10).

The method for bonding to polyethylene glycol via cysteine or mercapto are widely described in many publications (see Veronese, Biomaterials 2001, 22:405-417). People skilled in the art can link polyethylene glycol with mercapto-containing exendins.

Particularly, bonding via mercapto group can be achieved by way of the following:

1) Mercapto group originates from polypeptide chain. Achieved by incorporating the undermentioned amino acid:

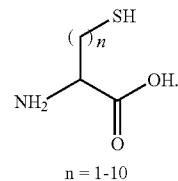

n = 1-10

By this time, polyethylene glycol should possess Michael addition acceptor, such as the double bond of maleimide, halogen or sulfonic acid esters substituted groups. Bonding is achieved by forming a thioether bond between polypeptide and polyethylene glycol.

2) Mercapto group originates from the side chain of the amino acid of a modified polypeptide, for example, mercapto group connects with the amino group of the lysine side chain. The amino acid with its side chain modified in the form of the following formula:

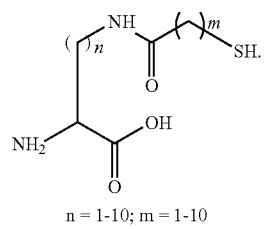

n = 1-10; m = 1-10

By this time, polyethylene glycol should possess Michael addition acceptor, such as the double bond in maleimide, halogen and sulfonic acid esters substituted groups; bonding is achieved by forming a thioether bond between polypeptide and polyethylene glycol.

3) Mercapto group originates from polyethylene glycol. By this time, the connection point in the polypeptide should contain Michael addition acceptor, such as the double bond in maleimide, halogen and sulfonate substituted groups. Bonding is achieved by forming a thioether bond between polypeptide and polyethylene glycol.

4) If both polyethylene glycol and polypeptide contain Mercapto groups, bonding can be achieved via the formation of asymmetric disulfide bond.

Preferably, covalent bond between polyethylene glycol and polypeptide of the present invention is achieved by the formation of a thioether bond in between. However, it is not the only way to link polyethylene glycol with the polypeptide sequence disclosed in the present invention. Other connection methods, such as acylation, reductive amination and oxime formation, are also included in the present invention.

The polypeptide derivatives listed in table 1 are suitable precursors for pegylation. However, they are included in the present invention by way of illustration only and the present invention is not limited to these sequences. In the sequence table, preferred sequences are selected from SEQ ID NO 80 to SEQ ID NO 141.

These pegylated exendins and polypeptide precursors thereof are amphoteric compounds, which can react with acids or bases to form salts. Commonly employed acids for salt formation are selected from hydrochloric acid, hydrobromic acid, hydriodic acid, sulfuric acid, phosphoric acid, p-toluenesulfonic acid, methanesulfonic acid, oxalic acid, p-bromobenzene sulfonic acid, carbonic acid, succinic acid, citric acid, benzoic acid, acetic acid, trifluoroacetic acid and the like. Examples of these salts include sulfate, pyrosulfate, hydrosulfate, sulfite, bisulphite, phosphate, hydrophosphate, dihydric phosphate, metaphosphate, pyrophosphate, hydrochloride, hydrobromide, hydriodate, acetate, propionate, caprate, caprylate, acrylate, formiate, isobutyrate, caproate, heptylate, propiolate, oxalate, malonate, succinate, suberate, sebacate, fumarate, maleate, butyne-1,4-dioate, hexyne-1,6-dioate, benzoate, chlorobenzoate, p-methylbenzoate, dinitrobenzoate, hydroxybenzoate, methoxybenzoate, phenylacetate, phenylpropionate, phenylbutyrate, citrate, lactate, r-hydroxybutyrate, glycerate, tartarate, methanesulfonate, propanesulfonate, naphthalene-1-sulfonate, naphthalene-2-sulfonate, mandelate and the like. Preferred acid addition salt is selected from hydrochloride, sulfate, acetate, trifluoroacetate; commonly employed bases for salt formation are selected from sodium hydroxide, potassium hydroxide, ammonia, potassium carbonate and the like.

The exendins of the present invention, particularly the pegylated exendins, can be used in preventing and treating type 2 diabetes, especially to those patients who present abnormal secretion caused by overweight or even obesity, due to their potential in recovering β-cell.

Accordingly, the present invention also relates a method for the treatment and prevention of type 2 diabetes, wherein effective dosage of the exendins of the present invention is administered to patients who in need thereof.

The exendins of the present invention can be used alone, and more suitably used in combination with other anti-diabetic medicaments (such as PPAR agonist, sulphonylurea, non-sulphonylurea (Secretagogues), α-glucosidase inhibitor, insulin sensitizer, insulin Secretagogues, glycogen-releasing inhibitor, insulin and other anti-obesity medicaments) in the treatment of diabetes.

Clinical dosage should be determined according to the actual therapeutic effectiveness of the various compounds, which is in the range of 0.0001 mg/kg to about 200 mg/kg body weight, preferably from 0.001 mg/kg to 20 mg/kg body weight, most preferably from 0.01 mg/kg to 1 mg/kg body weight. Routes of administration include injection methods (including intravenous, intramuscular and subcutaneous injection) or other continuous injection methods. These compounds can be formulated in a variety of preparations, and administered by conventional routes of administration, such as oral and transdermal administration, pulmonary, nasal, buccal spray, suppository administration and the like.

PREFERRED EMBODIMENTS OF THE INVENTION

Figure 1:
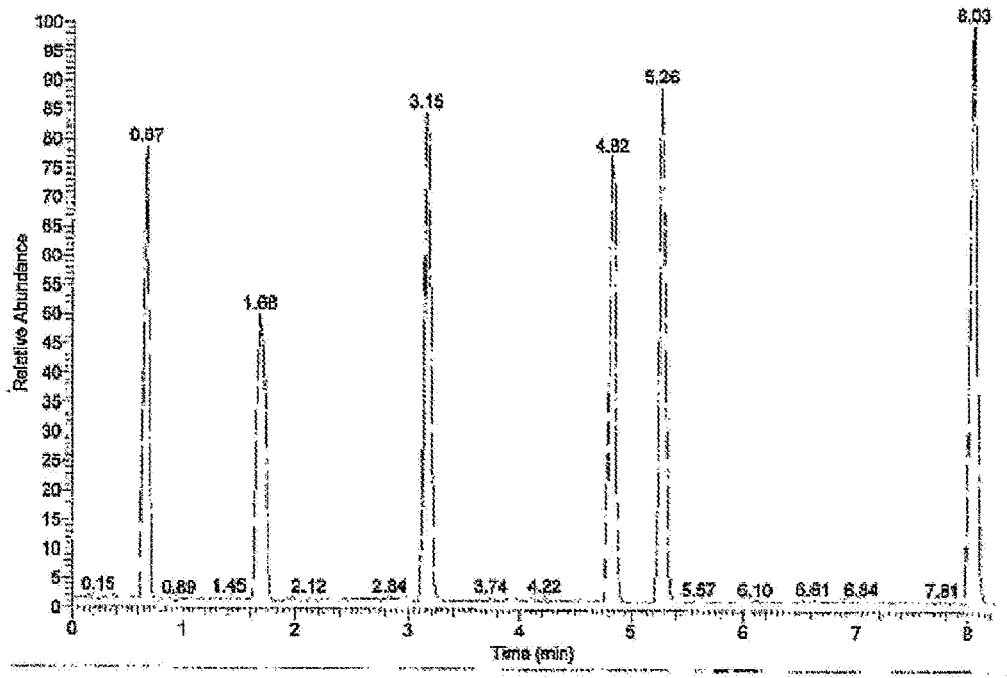
FIG. 1 shows the LC-MS spectrum of SEQ ID No 95.
Figure 1:
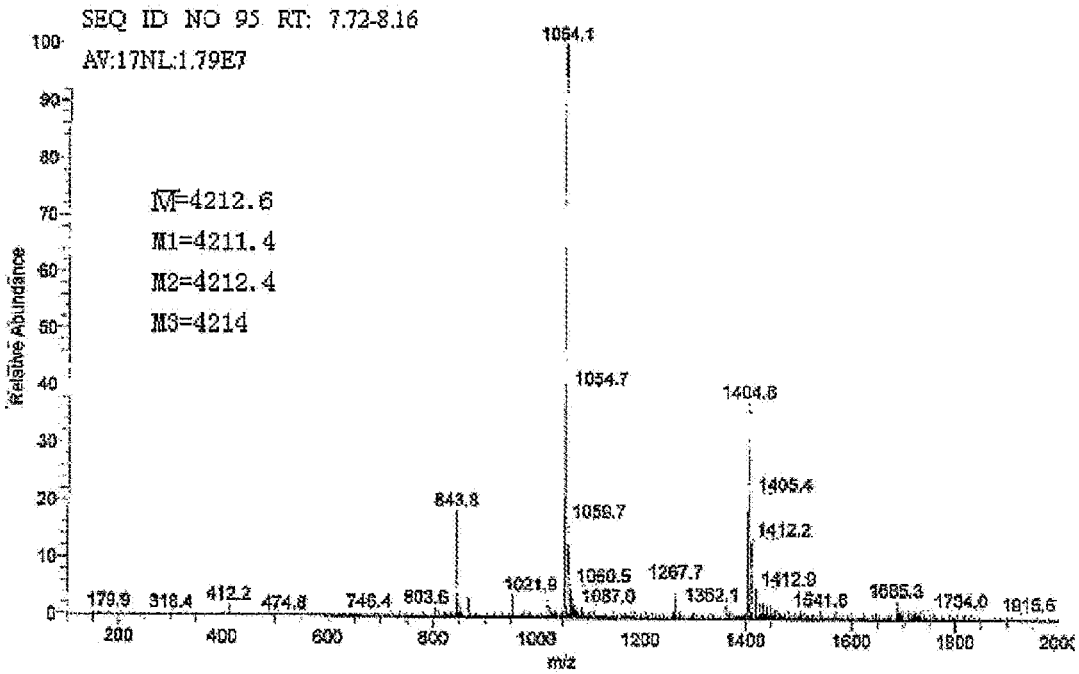
Figure 2:
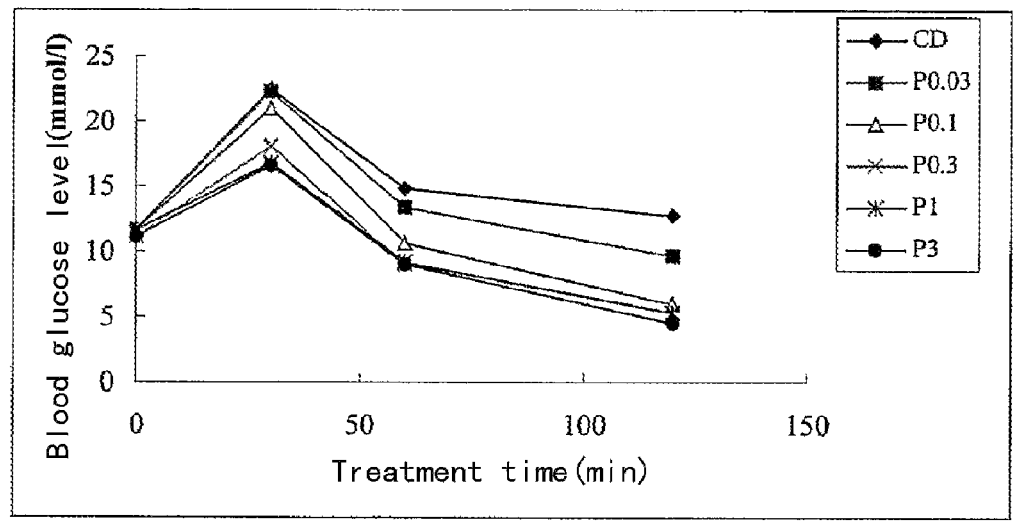
FIG. 2 shows the influence of PEG-EX-4 analogue on Glucose Tolerance of db/db mice on the first day of subcutaneous injection.
Figure 3:
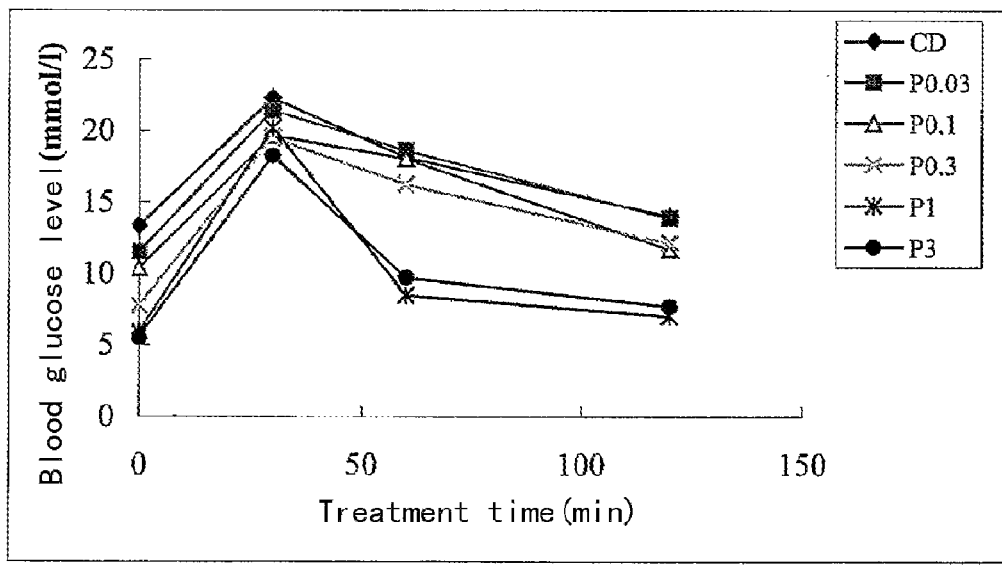
FIG. 3 shows the influence of PEG-EX-4 analogue on Glucose Tolerance of db/db mice on the third day after subcutaneous injection.
Figure 4:
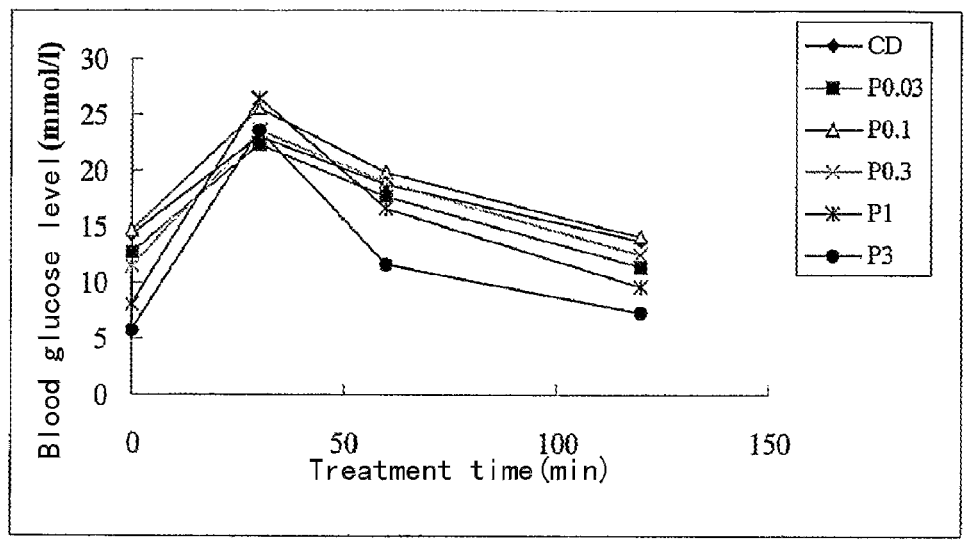
FIG. 4 shows the influence of PEG-EX-4 analogue on Glucose Tolerance of db/db mice on the sixth day after subcutaneous injection.
Figure 5:
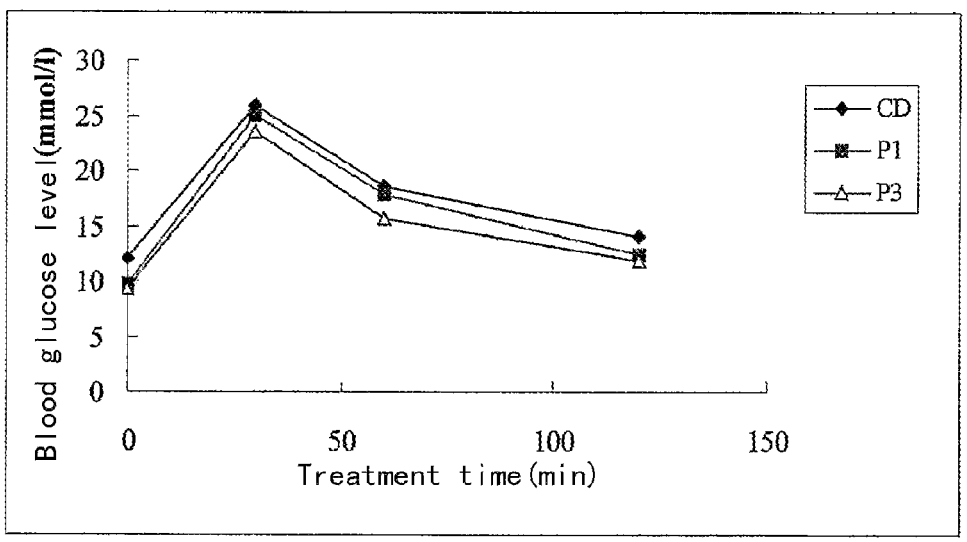
FIG. 5 shows the influence of PEG-EX-4 analogue on Glucose Tolerance of db/db mice on the ninth day after subcutaneous injection.

The examples provided hereinafter assist in better understanding the present invention, which are not intended to limit the present invention.

Example 1

Solid-phase Synthesis of Compound SEQ ID No 95 of the Present Invention (1) Amino Acid Monomers Used in the Synthesis Fmoc-His(Trt)-OH, Fmoc-dAla-OH, Fmoc-Gly-OH, Fmoc-Glu(OtBu)-OH, Fmoc-Thr(tBu)-OH, Fmoc-Phe-OH, Fmoc-Ser(tBu)-OH, Fmoc-Asp(OtBu)-OH, Fmoc-Leu-OH, Fmoc-Lys(Boc)-OH, Fmoc-Gln(Trt)-OH, Fmoc-Nle-OH, Fmoc-Ala-OH, Fmoc-Val-OH, Fmoc-Arg (pbf)-OH, Fmoc-Ile-OH, Fmoc-Trp(Boc)-OH, Fmoc-Asn(Trt)-OH, Fmoc-Pro-OH, Fmoc-Cys(Trt)-OH Abbreviation of the above: Fmoc: 9-fluorenylmethoxycarbonyl; Boc: tert-butoxycarbonyl; Trt: trityl; OtBu: t-butoxy; tBu: t-butyl.

(2) The Reagents used: N,N-diisopropylethylamine, diisopropylcarbodiimide (DIC),
N,N-dimethylformamide (DMF), dichloromethane, hexahydropyridine, 1-hydroxybenzotriazole, Rink amide resin, ninhydrin, methanol, anisole, triisopropylsilane, trifluoroacetic acid.

(3) Experimental Procedure

A. Synthesis: To 0.5 g (0.25 mmole) Rink amide resin in a reactor vessel, 1 mmol amino acid was added, activation was conducted with DIC/HOBT method, and the synthesis was conducted starting from C-terminal to N-terminal according to the polypeptide sequence. The reaction was conducted at 25° C. (room temperature) following the operating procedure below:

1. Fmoc group was deprotected by treating with 20% hexahydropyridine in DMF, 10 min for each time.
2. The resins were washed with 10 mL DMF for three times, and then dried with pump.
3. The protected amino acid (1 mmol) and HOBT (1 mmol) were weighed out and then dissolved in 10 ml DMF followed by addition of DIC (1 mmol), and then activated for 10 minutes.

4. The activated amino acid solution was added to the reactor vessel and then shaked for 1 hour.
5. The resins were washed with DMF for three times, and then dried with pump.
6. Steps 1-5 were repeated for the next cycle in the case of negative result for the ninhydrin test, whereas steps 3-5 were repeated in the case of positive result for the ninhydrin test.

After the synthesis of polypeptides, the resins were completely washed with methanol and then dried in air.

B. Deprotection of the Protecting Groups and Cleavage of Polypeptides

To 1 g resin having the polypeptide in the reactor vessel was added the cleavage solution in the following proportion.

| Solvents | Amount (mL) |
|---|---|
| Anisole | 2 |
| Methanol | 2 |
| Triisopropylsilane | 2 |
| Trifluoroacetic Acid | 6 |

The content in reactor vessel was shaked for 2 hours at room temperature, and then filtered. The filtrate was collected and the resins were washed with a slight amount of acetic acid. The collection fluids were combined. After concentration, ethylether was added and precipitate was generated. Precipitate was washed with a slight amount of ethylether to afford the crude product.

C. Purification with High Performance Liquid Chromatography and Lyophilization

The resulting crude product was dissolved in 10% acetic acid solution, the solution was injected into the HPLC system for purification, followed by lyophilization to afford the product. The resulting polypeptide was analyzed and confirmed as the desired compound using Chromatography-Mass Spectrometry.

Column: luna C18 (2), 5μ, 100 Å
Detective wavelength: λ=220 nm, Waters preparative system
Gradient: (TFA: trifluoroacetic acid)

| T (minute) | A: (0.05% TFA) CH$_3$CN | B: (0.05TFA) H$_2$O |
|---|---|---|
| 0 | 10% | 90% |
| 20 | 45% | 55% |
| 30 | 45% | 55% |
| 30.1 | 10% | 90% |

The molecular weight of the resulting compound: 4212.6 g/mol; the theoretical molecular weight: 4213 g/mol.

FIG. 1: LC-MS spectrum of SEQ ID No 95

Example 2

Method for Pegylation of Exendins

Pegylation of exendins can be conducted with conventional method. Pegylation of peptides is achieved by modifying mercapto group in the formation of a thioether bond between polyethylene glycol and peptide. To be more particular, one or more cysteines were added to the carboxyl-terminal of the optimized Exendin-4 derivatives, followed by pegylation conducted by using polyethylene glycol which contains the Maleimide functional group. Thioether bond was formed after Michael addition reaction, and thereby polypeptide was covalently bonded with the polyethylene glycol. In general, the desired polypeptide was dissolved in 0.1M phosphate buffer solution, followed by addition of polyethylene glycol under anaerobic environment. The molar ratio of polyethylene glycol to polypeptide was 1:1 and the pH of the reaction was 6 to 7.5. Oxidation of the mercapto group may be reduced by addition of EDTA to the reaction solution. After two hours, the reaction solution was purified with reverse-phase HPLC system. Excess or unreacted polyethylene glycol was removed by ion-exchange chromatography. The molecular weight of the resulting product was analyzed and confirmed by mass spectrum. The purity of the product was analyzed with RP-HPLC and Gel-chromatography. Taking the modification of SEQ ID NO 95 as an example, when 43KD PEG was employed in modification, the yield was 70-90% (based on polyethylene glycol).

Example 3

Test for the Stability of the Polypeptide

The Exendin-4 derivatives of the present invention possess the optimized enzymatic and chemical stability. The following method was used to determine the chemical stability of some polypeptides in the present invention.

1 mg of each sample was dissolved in a buffer solution, which contains 150 mM sodium chloride and 20 mM phosphate, from which a solution of concentration of 4 mg/ml was prepared and its pH is 8.0. The testing sample solutions were placed in a thermostat of 40° C. LC-MS was used to determine the purity of polypeptide. Correlation between the reduction ratio of the main peak area and time reflects the chemical stability of the polypeptide.

TABLE 2

Determination of the stability of Exendin-4 based compounds

| Purity (%) | 0 day | 5$^{th}$ day | 10$^{th}$ day | 15$^{th}$ day |
|---|---|---|---|---|
| Sample 1 | 98.2 | 88.0 | 81.6 | 76.2 |
| Sample 2 | 98 | 93.1 | 90.4 | 88.2 |
| Sample 3 | 98.9 | 98.8 | 98.8 | 98.8 |
| Sample 4 | 99.7 | 99.4 | 99.0 | 99.3 | wherein, sample 1 is Exendin-4 as control, and the sequence is:
His-Gly$^2$-Glu-Gly-Thr-Phe-Thr-Ser-Asp-Leu-Ser-Lys-Gln-Met$^{14}$-Glu-Glu-Glu-Ala-Val-Arg-Leu-Phe-Ile-Glu-Trp-Leu-Lys-Asn$^{28}$-Gly-Gly-Pro-Ser-Ser-Gly-Ala-Pro-Pro-Pro-Ser$^{39}$.

Sample 2: 2#Gly in sample 1 was substituted with d-Ala, and 39# was substituted with Cys.

Sample 3: 2#Gly in sample 1 was substituted with d-Ala, and 14# Met was substituted with Nle, 28#Asn was substituted with Gln.

Sample 4: sample 2 is covalently bonded with PEG40K via Cys at the C-terminal of sample 2; wherein all the C-terminal of samples 1-4 are amide.

Conclusion:

The sequence of sample 1 is a polypeptide sequence that can be isolated from nature. His-Gly residue at the N-terminal is an ideal substrate for dipeptidase and Met that contained in sample 1 readily undergoes oxidization, and also Asn undergoes self-reaction readily, which render sample 1 unstable.

Substitution at position 2, or 14, or 28 greatly improve the stability of the peptides; in addition, substitution at all the 3 positions allows a greater improvement in the stability of the peptides than substitution of His-Gly with His-dAla alone. Although sample 2 is not very stable, it become very stable after bonding with PEG40K (i.e. sample 4), which shows that PEG is useful in enhancing the stability of polypeptide.

Example 4

Formulation

| PEG-EX-4 analogue | 5 g |
|---|---|
| m-Cresol | 0.04 g |
| Iced acetic acid | Appropriate amount |
| Iced sodium acetate | Appropriate amount |
| Injection water | Appropriate amount |

100 ml/100 bottles

Sterile Preparation

Experimental Example 1

Oral Glucose Tolerance Test of Polypeptide

Polypeptide of SEQ ID NO 25 was modified with polyethylene glycol of molecular weight of about 40000 (sample 5). Oral glucose tolerance test was then conducted with normal mice and the results were presented in the following tables: Table 1. Subcutaneous injections of sample 5 with various dosages were administered to normal mice. The influences on the oral glucose tolerance and the area under the curve of the blood glucose level on the first day and the third day after subcutaneous injections were given.
(The First Day)

Experimental Example 2

Influence of PEG-EXENDIN-4 (PEG-EX-4) Analogue on Type 2 Diabetes db/db Mice

1. Testing animals: species, strains: db/db mice, source: Model Animal Center of Nanjing University, body weights of mice: 35 g-50 g, male and female in half. Numbers of animal: 45, 5-6 mice in each group. Rearing conditions: rearing in SPF grade animal housing, temperature: 22° C.-24° C., humidity: 45%-80%, illumination: 150 Lx-300 Lx, under the 12 h-light and 12 h-dark cycle condition.
2. Test Method:
Dosage setting up: 5 administration groups: 0.03, 0.1, 0.3, 1 and 3 mg/kg; and a blank control group as well; route of administration: subcutaneous injection; volume of administration: 0.05 ml/kg body weight.
(1) Influence on Blood Glucose Level of Non-Fasting db/db Mice
According to the non-fasting blood glucose level and body weight of mice, db/db mice were divided into blank control group and another 5 groups to be administered with PEG-EX-4 analogue, 6 mice in each group, and male and female in half. Animals in each group were administered with the testing drug and physiological saline, respectively, by a single subcutaneous injection. Blood glucose level was detected before administration and also 1, 2, 4, 8, 24 hours after administration. Thereafter, the non-fasting blood glucose level was detected every 24 hours. The lasting time for the reduction of blood glucose level of the testing drugs as well as the variation in food intake and body weights after administration were observed.
(2) Influence on Blood Glucose Level of Fasting db/db Mice
According to the non-fasting, fasting blood glucose level and body weight of mice, db/db mice were divided into blank control group and another 5 groups to be administered with

| | Blood Glucose level (mg/dl) | | | | AUC |
|---|---|---|---|---|---|
| Group | 0 min | 30 min | 60 min | 120 min | (mg · h/dl) |
| physiological saline | 129.7 ± 8.1 | 223.2 ± 33.4 | 167.7 ± 34.5 | 98.1 ± 12.1 | 318.8 ± 42.9 |
| Sample 5 (20) | 116.6 ± 10.8 | 95.7 ± 9.9*** | 88.9 ± 28.6*** | 65.4 ± 5.1*** | 176.4 ± 22.0*** |
| Sample 5 (80) | 122.2 ± 9.1 | 92.1 ± 12.4* | 76.7 ± 8.7* | 64.9 ± 7.5* | 166.6 ± 16.7* | v.s Con
***$P < 0.001$;
n = 10

(The Third Day)

| | Blood glucose level (mg/dl) | | | | AUC |
|---|---|---|---|---|---|
| Group | 0 min | 30 min | 60 min | 120 min | (mg · h/dl) |
| physiological saline | 97.3 ± 19.8 | 193.6 ± 35.3 | 171.0 ± 46.7 | 91.8 ± 18.8 | 295.3 ± 54.0 |
| Sample 5 (20) | 96.2 ± 8.6 | 172.8 ± 33.2 | 132.1 ± 12.4* | 88.3 ± 7.8 | 253.6 ± 24.4* |
| Sample 5 (80) | 89.5 ± 9.3 | 149.3 ± 32.4 | 108.6 ± 8.8* | 77.1 ± 8.4* | 217.0 ± 21.9*** | v.s Con,
*$P < 0.05$,
**$P < 0.01$,
***$P < 0.001$;
n = 10

PEG-EX-4 analogue, 6 mice in each group, and male and female in half. After fasting for 5 hours, animals in each group were administered with the testing drug and physiological saline, respectively, by a single subcutaneous injection. Blood glucose level was detected before administration and also 1, 2 hours after administration. Thereafter, the non-fasting and fasting blood glucose level was detected every 24 hours. The lasting time for the reduction of blood glucose level of the testing drug as well as the variation in food intake and body weights after administration were observed.

(3) Influence on Fasting Blood Glucose Level of db/db Mice

According to the fasting blood glucose level and body weight of mice, db/db mice were divided into blank control group and another 5 groups to be administered with PEG-EX-4 analogue, and 5 mice in each group. After fasting for 5 hours, animals in each group were administered with the testing drug and physiological saline, respectively, by a single subcutaneous injection. 2.5 g/kg of glucose was taken orally 15 minutes after the above administration. After that, blood glucose level was detected immediately after taking glucose (0 min) and also 30, 60 and 120 minutes after taking glucose. Oral glucose tolerance test was conducted on the third day, sixth day and ninth day, respectively, after the drug administration. The influences of the testing drug on the glucose tolerance of db/db as well as its lasting time and the variation in food intake and body weights after administration were observed.

3. Test Results: the Results for the Influences of Peg-Ex-4 Analogue on Blood Glucose Level of Db/Db Mice were Presented and Summarized in FIGS. 2-5 and Tables 1-6.

(1) Influence on Blood Glucose Level of Fasting and Non-Fasting db/db Mice

TABLE 1

Influence of subcutaneous injection of PEG-EX-4 analogue on fasting blood glucose level of db/db mice (mean value ± SD, n = 6)

| Group | Dosage µg/kg | Before administration 0 | After administration (hrs) | | | |
|---|---|---|---|---|---|---|
| | | | 1 | 2 | 24 | 48 |
| Blank control | — | 11.53 ± 5.73 | 11.77 ± 6.69 | 10.27 ± 7.16 | 11.07 ± 4.46 | 10.07 ± 4.66 |
| PEG-EX-4 analogue | 0.03 | 11.28 ± 2.68 | 8.40 ± 2.02 | 6.75 ± 2.02 | 8.58 ± 2.17 | 10.97 ± 4.09 |
| | 0.1 | 11.08 ± 5.65 | 6.70 ± 4.35 | 5.85 ± 4.60 | 9.12 ± 4.84 | 11.23 ± 5.89 |
| | 0.3 | 11.15 ± 3.33 | 5.13 ± 1.83* | 3.78 ± 0.73 | 5.80 ± 2.63* | 6.77 ± 2.18 |
| | 1 | 11.42 ± 3.74 | 4.73 ± 1.91* | 3.78 ± 0.83 | 3.93 ± 0.95** | 5.03 ± 1.36* |
| | 3 | 11.00 ± 3.66 | 3.62 ± 1.07* | 3.05 ± 0.67* | 4.03 ± 1.20** | 3.65 ± 0.76** |

| Group | Dosage µg/kg | After administration (hrs) | | | | | |
|---|---|---|---|---|---|---|---|
| | | 72 | 96 | 120 | 144 | 168 | 192 |
| Blank control | — | 11.53 ± 6.33 | 14.90 ± 6.81 | 14.32 ± 6.61 | 14.38 ± 5.10 | 13.53 ± 7.04 | 13.20 ± 6.27 |
| PEG-EX-4 analogue | 0.03 | — | — | — | — | — | — |
| | 0.1 | — | — | — | — | — | — |
| | 0.3 | 8.27 ± 2.59 | 10.60 ± 3.04 | 11.15 ± 4.98 | 11.70 ± 3.76 | 12.60 ± 3.84 | — |
| | 1 | 7.15 ± 3.10 | 8.07 ± 2.29* | 8.13 ± 1.21* | 10.75 ± 1.87 | 11.07 ± 2.65 | 12.12 ± 1.31 |
| | 3 | 5.80 ± 2.19 | 6.03 ± 1.09* | 5.70 ± 2.23* | 7.70 ± 2.64* | 9.17 ± 2.32 | 11.43 ± 2.26 |

TABLE 2

Influence of subcutaneous injections of PEG-EX-4 analogue on daily non-fasting blood glucose level of db/db mice (mean value ± SD, n = 6)

| Group | Dosage µg/kg | Before administration 0 | After administration (hrs) | | | | | | |
|---|---|---|---|---|---|---|---|---|---|
| | | | 24 | 48 | 72 | 96 | 120 | 144 | 168 |
| Blank control | — | 14.70 ± 6.87 | 17.18 ± 4.47 | 15.22 ± 5.16 | 15.45 ± 6.02 | 16.13 ± 6.96 | 15.12 ± 8.05 | 15.45 ± 5.91 | 15.25 ± 6.17 |
| PEG-EX-4 analogue | 0.03 | 14.73 ± 5.00 | 13.42 ± 4.19 | 12.88 ± 4.50 | 15.92 ± 5.39 | — | — | — | — |
| | 0.1 | 14.52 ± 6.01 | 15.32 ± 6.62 | 16.22 ± 3.61 | — | — | — | — | — |
| | 0.3 | 14.08 ± 2.66 | 11.35 ± 5.96 | 11.57 ± 3.07 | 15.78 ± 3.56 | 15.17 ± 2.60 | 14.17 ± 4.48 | 13.53 ± 4.50 | 13.72 ± 3.89 |
| | 1 | 14.30 ± 3.79 | 7.02 ± 2.49*** | 9.17 ± 4.45 | 13.73 ± 7.09 | 13.63 ± 5.48 | 12.28 ± 4.30 | 12.50 ± 5.06 | 12.68 ± 2.73 |
| | 3 | 14.10 ± .86 | 5.65 ± 1.73*** | 7.48 ± .15* | 9.87 ± 4.74 | 13.42 ± 4.89 | 11.92 ± 5.10 | 12.93 ± 3.72 | 15.27 ± 2.58 |

(2) Influence on fasting blood glucose level of db/db mice

TABLE 3

Influences of PEG-EX-4 analogue on the glucose tolerance of db/db mice on the first day after subcutaneous injection (mean value ± SD, n = 5).

| Group | Dosage μg/kg | Before administration 0 | After glucose administration (mmol/l) 30 | 60 | 120 | AUC |
|---|---|---|---|---|---|---|
| Blank control | — | 11.66 ± 4.74 | 22.36 ± 5.76 | 14.84 ± 7.40 | 12.74 ± 5.10 | 31.60 ± 11.67 |
| PEG-EX-4 analogue | 0.03 | 11.64 ± 4.51 | 22.28 ± 6.34 | 13.44 ± 7.47 | 9.62 ± 8.27 | 28.94 ± 13.98 |
|  | 0.1 | 11.54 ± 1.80 | 20.92 ± 2.99 | 10.66 ± 1.86 | 6.02 ± 1.25* | 24.35 ± 3.51 |
|  | 0.3 | 11.18 ± 4.62 | 18.10 ± 1.67 | 9.06 ± 2.23 | 5.34 ± 1.34* | 21.31 ± 4.01 |
|  | 1 | 11.54 ± 2.50 | 16.82 ± 2.38 | 9.12 ± 4.60 | 5.26 ± 2.54* | 20.77 ± 6.28 |
|  | 3 | 11.18 ± 4.37 | 16.54 ± 4.40 | 9.10 ± 3.21 | 4.44 ± 1.74** | 20.11 ± 5.98 |

TABLE 4

Influence of PEG-EX-4 analogue on glucose tolerance of db/db mice on the third day after subcutaneous injection (mean value ± SD, n = 5)

| Group | Dosage μg/kg | Before administration 0 | After glucose administration (mmol/l) 30 | 60 | 120 | AUC |
|---|---|---|---|---|---|---|
| Blank control | — | 13.34 ± 6.85 | 22.28 ± 5.59 | 18.16 ± 6.55 | 14.06 ± 4.94 | 35.13 ± 11.22 |
| PEG-EX-4 analogue | 0.03 | 11.50 ± 4.75 | 21.40 ± 4.06 | 18.64 ± 5.97 | 13.94 ± 6.10 | 34.53 ± 10.64 |
|  | 0.1 | 10.38 ± 3.65 | 19.66 ± 7.27 | 18.06 ± 2.45 | 11.72 ± 4.58 | 31.83 ± 8.03 |
|  | 0.3 | 7.72 ± 2.77 | 19.52 ± 2.40 | 16.24 ± 5.68 | 12.16 ± 5.76 | 29.95 ± 8.80 |
|  | 1 | 5.88 ± 0.92* | 20.18 ± 2.82 | 8.50 ± 2.88* | 7.04 ± 1.71* | 21.46 ± 4.02* |
|  | 3 | 5.50 ± 2.29* | 18.24 ± 5.05 | 9.74 ± 5.57 | 7.72 ± 4.98 | 21.66 ± 9.51 |

TABLE 5

Influence of PEG-EX-4 analogue on glucose tolerance of db/db mice on the sixth day after subcutaneous injection (mean value ± SD, n = 5)

| Group | Dosage μg/kg | Before administration 0 | After glucose administration (mmol/l) 30 | 60 | 120 | AUC |
|---|---|---|---|---|---|---|
| Blank control | — | 14.20 ± 6.56 | 22.96 ± 2.86 | 18.70 ± 7.15 | 13.70 ± 7.12 | 35.91 ± 11.33 |
| PEG-EX-4 analogue | 0.03 | 12.62 ± 7.38 | 22.28 ± 4.45 | 17.62 ± 5.40 | 11.50 ± 6.38 | 33.26 ± 10.59 |
|  | 0.1 | 14.60 ± 3.49 | 25.62 ± 2.45 | 19.76 ± 2.56 | 14.12 ± 2.05 | 38.34 ± 4.32 |
|  | 0.3 | 11.50 ± 4.55 | 23.58 ± 1.89 | 18.94 ± 3.86 | 12.42 ± 4.99 | 35.08 ± 7.04 |
|  | 1 | 8.12 ± 1.22 | 26.34 ± 2.09 | 16.54 ± 3.65 | 9.68 ± 2.63 | 32.45 ± 4.92 |
|  | 3 | 5.80 ± .48* | 23.66 ± 4.50 | 11.66 ± 4.37 | 7.28 ± 2.40 | 25.67 ± 6.94 |

TABLE 6

Influence of PEG-EX-4 analogue on glucose tolerance of db/db mice on the ninth day after subcutaneous injection (mean value ± SD, n = 5)

| Group | Dosage μg/kg | Before administration 0 | After glucose administration (mmol/l) 30 | 60 | 120 | AUC |
|---|---|---|---|---|---|---|
| Blank control | — | 12.04 ± 8.47 | 25.90 ± 4.16 | 18.52 ± 8.29 | 14.04 ± 7.91 | 36.87 ± 14.14 |
| PEG-EX-4 analogue | 1 | 9.60 ± 1.16 | 24.86 ± 1.67 | 17.90 ± 2.92 | 12.28 ± 4.08 | 34.40 ± 4.89 |
|  | 3 | 9.36 ± 3.66 | 23.46 ± 2.41 | 15.60 ± .02 | 11.84 ± 4.35 | 31.69 ± 6.64 |

*$P < 0.05$;
**$P < 0.01$;
***$P < 0.001$, in comparison with blank control group

Experimental Example 3
Preliminary Testing Results of the Influence of Peg-Exendin-4 (Peg-Ex-4) Analogue on Blood Glucose Level of KKAy Mice 1. Test Methods:

Single subcutaneous injections of PEG-EX-4 analogue at various dosages were administered to normal mice. Variation in blood glucose level at different times after injection was detected.

Figure 6:
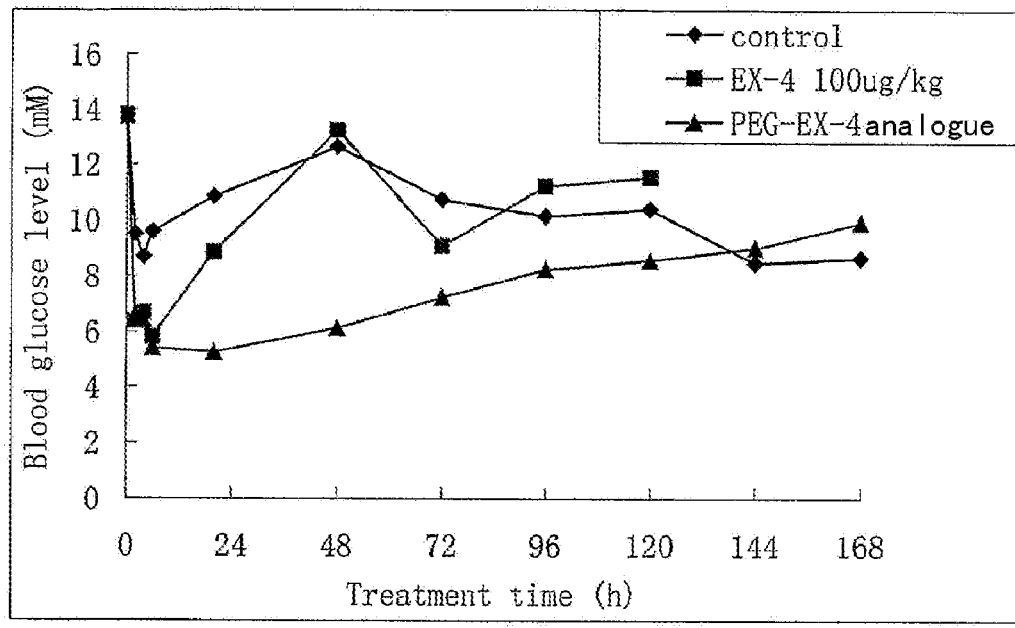
FIG. 6 shows the reduction effect on blood glucose level of mice after subcutaneous injection of PEG-EX-4 analogue (1100 μg/kg).

2. Test Results:

(1) See FIG. 6, the reduced blood glucose level of KKay mice lasts for 3-4 days after subcutaneous injection of PEG-EX-4 analogue (1100 g/kg).

Figure 7:
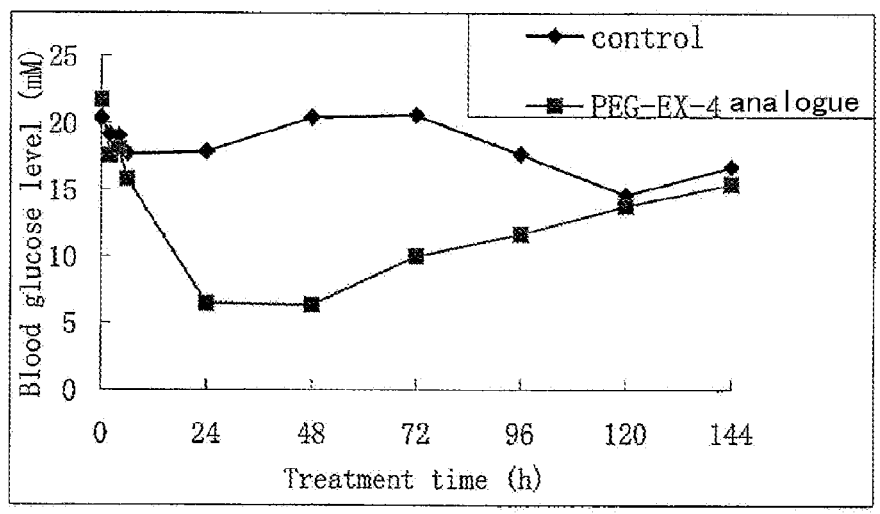
FIG. 7 shows the reduction effect on blood glucose level of mice after subcutaneous injection of PEG-EX-4 analogue (3300 μg/kg).

(2) See FIG. 7, the reduced blood glucose level of KKay mice lasts for 3-4 days after subcutaneous injection of PEG-EX-4 analogue (3300 g/kg).

TABLE 7

The amino acid sequences of the said long-lasting exendins of the present invention were given.

| Series Number | Sequences | SEQ ID NO |
|---|---|---|
| HR1 | HGEGTFTSDL SKQMEEEAVR LFIEWLKNGG PSSGAPPPS | 4 |
| HR2 | HGEGTFTSDL SKQMEEEAVR LFIEWLKNGG PSSGAPPPC | 5 |
| HR3 | HGEGTFTSDL SKQMEEEAVR LFIEWLKNGG PSSGAPPPCC | 6 |
| HR4 | HGEGTFTSDL SKQMEEEAVR LFIEWLKNGG PSSGAPPPhC | 7 |
| HR5 | HGEGTFTSDL SKQMEEEAVR LFIEWLKNGG PSSGAPPPhChC | 8 |
| HR6 | HGEGTFTSDL SKQMEEEAVR LFIEWLKNGG PSSGAPPPK* | 9 |
| HR7 | HGEGTFTSDL SKQMEEEAVR LFIEWLKNGG PSSGAPPPK*K* | 10 |
| HR8 | HGEGTFTSDL SKQMEEEAVR LFIEWLKNGG PSSGAPPPC-$NH_2$ | 11 |
| HR9 | HGEGTFTSDL SKQMEEEAVR LFIEWLKNGG PSSGAPPPCC-$NH_2$ | 12 |
| HR10 | HGEGTFTSDL SKQMEEEAVR LFIEWLKNGG PSSGAPPPhC-$NH_2$ | 13 |
| HR11 | HGEGTFTSDL SKQMEEEAVR LFIEWLKNGG PSSGAPPPhChC-$NH_2$ | 14 |
| HR12 | HGEGTFTSDL SKQMEEEAVR LFIEWLKNGG PSSGAPPPK*-$NH_2$ | 15 |
| HR13 | HGEGTFTSDL SKQMEEEAVR LFIEWLKNGG PSSGAPPPK*K*-$NH_2$ | 16 |
| HR14 | HdAEGTFTSDL SKQMEEEAVR LFIEWLKNGG PSSGAPPPS | 17 |
| HR15 | HdAEGTFTSDL SKQMEEEAVR LFIEWLKNGG PSSGAPPPC | 18 |
| HR16 | HdAEGTFTSDL SKQMEEEAVR LFIEWLKNGG PSSGAPPPCC | 19 |
| HR17 | HdAEGTFTSDL SKQMEEEAVR LFIEWLKNGG PSSGAPPPhC | 20 |
| HR18 | HdAEGTFTSDL SKQMEEEAVR LFIEWLKNGG PSSGAPPPhChC | 21 |
| HR19 | HdAEGTFTSDL SKQMEEEAVR LFIEWLKNGG PSSGAPPPK* | 22 |
| HR20 | HdAEGTFTSDL SKQMEEEAVR LFIEWLKNGG PSSGAPPPK*K* | 23 |
| HR21 | HdAEGTFTSDL SKQMEEEAVR LFIEWLKNGG PSSGAPPPS-$NH_2$ | 24 |
| HR22 | HdAEGTFTSDL SKQMEEEAVR LFIEWLKNGG PSSGAPPPC-$NH_2$ | 25 |
| HR23 | HdAEGTFTSDL SKQMEEEAVR LFIEWLKNGG PSSGAPPPCC-$NH_2$ | 26 |
| HR24 | HdAEGTFTSDL SKQMEEEAVR LFIEWLKNGG PSSGAPPPhC-$NH_2$ | 27 |
| HR25 | HdAEGTFTSDL SKQMEEEAVR LFIEWLKNGG PSSGAPPPhChC-$NH_2$ | 28 |
| HR26 | HdAEGTFTSDL SKQMEEEAVR LFIEWLKNGG PSSGAPPPK*-$NH_2$ | 29 |
| HR27 | HdAEGTFTSDL SKQMEEEAVR LFIEWLKNGG PSSGAPPPK*K*-$NH_2$ | 30 |
| HR28 | HGEGTFTSDL SKQNleEEEAVR LFIEWLKNGG PSSGAPPPS | 31 |
| HR29 | HGEGTFTSDL SKQNleEEEAVR LFIEWLKNGG PSSGAPPPC | 32 |
| HR30 | HGEGTFTSDL SKQNleEEEAVR LFIEWLKNGG PSSGAPPPCC | 33 |
| HR31 | HGEGTFTSDL SKQNleEEEAVR LFIEWLKNGG PSSGAPPPhC | 34 |

TABLE 7-continued

The amino acid sequences of the said long-lasting exendins of the present invention were given.

| Series Number | Sequences | SEQ ID NO |
|---|---|---|
| HR32 | HGEGTFTSDL SKQNleEEEAVR LFIEWLKNGG PSSGAPPPhChC | 35 |
| HR33 | HGEGTFTSDL SKQNleEEEAVR LFIEWLKNGG PSSGAPPPK* | 36 |
| HR34 | HGEGTFTSDL SKQNleEEEAVR LFIEWLKNGG PSSGAPPPK*K* | 37 |
| HR35 | HGEGTFTSDL SKQNleEEEAVR LFIEWLKNGG PSSGAPPPS-NH$_2$ | 38 |
| HR36 | HGEGTFTSDL SKQNleEEEAVR LFIEWLKNGG PSSGAPPPC-NH$_2$ | 39 |
| HR37 | HGEGTFTSDL SKQNleEEEAVR LFIEWLKNGG PSSGAPPPCC-NH$_2$ | 40 |
| HR38 | HGEGTFTSDL SKQNleEEEAVR LFIEWLKNGG PSSGAPPPhC-NH$_2$ | 41 |
| HR39 | HGEGTFTSDL SKQNleEEEAVR LFIEWLKNGG PSSGAPPPhChC-NH$_2$ | 42 |
| HR40 | HGEGTFTSDL SKQNleEEEAVR LFIEWLKNGG PSSGAPPPK*-NH$_2$ | 43 |
| HR41 | HGEGTFTSDL SKQNleEEEAVR LFIEWLKNGG PSSGAPPPK*K*-NH$_2$ | 44 |
| HR42 | HGEGTFTSDL SKQMEEEAVR LFIEWLKQGG PSSGAPPPS | 45 |
| HR43 | HGEGTFTSDL SKQMEEEAVR LFIEWLKQGG PSSGAPPPC | 46 |
| HR44 | HGEGTFTSDL SKQMEEEAVR LFIEWLKQGG PSSGAPPPCC | 47 |
| HR45 | HGEGTFTSDL SKQMEEEAVR LFIEWLKQGG PSSGAPPPhC | 48 |
| HR46 | HGEGTFTSDL SKQMEEEAVR LFIEWLKQGG PSSGAPPhChC | 49 |
| HR47 | HGEGTFTSDL SKQMEEEAVR LFIEWLKQGG PSSGAPPPK* | 50 |
| HR48 | HGEGTFTSDL SKQMEEEAVR LFIEWLKQGG PSSGAPPPK*K* | 51 |
| HR49 | HGEGTFTSDL SKQMEEEAVR LFIEWLKQGG PSSGAPPPS-NH$_2$ | 52 |
| HR50 | HGEGTFTSDL SKQMEEEAVR LFIEWLKQGG PSSGAPPPC-NH$_2$ | 53 |
| HR51 | HGEGTFTSDL SKQMEEEAVR LFIEWLKQGG PSSGAPPPCC-NH$_2$ | 54 |
| HR52 | HGEGTFTSDL SKQMEEEAVR LFIEWLKQGG PSSGAPPPhC-NH$_2$ | 55 |
| HR53 | HGEGTFTSDL SKQMEEEAVR LFIEWLKQGG PSSGAPPPhChC-NH$_2$ | 56 |
| HR54 | HGEGTFTSDL SKQMEEEAVR LFIEWLKQGG PSSGAPPPK*-NH$_2$ | 57 |
| HR55 | HGEGTFTSDL SKQMEEEAVR LFIEWLKQGG PSSGAPPPK*K*-NH$_2$ | 58 |
| HR56 | HdAEGTFTSDL SKQNleEEEAVR LFIEWLKNGG PSSGAPPPS | 59 |
| HR57 | HdAEGTFTSDL SKQNleEEEAVR LFIEWLKNGG PSSGAPPPC | 60 |
| HR58 | HdAEGTFTSDL SKQNleEEEAVR LFIEWLKNGG PSSGAPPPCC | 61 |
| HR59 | HdAEGTFTSDL SKQNleEEEAVR LFIEWLKNGG PSSGAPPPhC | 62 |
| HR60 | HdAEGTFTSDL SKQNleEEEAVR LFIEWLKNGG PSSGAPPPhChC | 63 |
| HR61 | HdAEGTFTSDL SKQNleEEEAVR LFIEWLKNGG PSSGAPPPK* | 64 |
| HR62 | HdAEGTFTSDL SKQNleEEEAVR LFIEWLKNGG PSSGAPPPK*K* | 65 |
| HR63 | HdAEGTFTSDL SKQNleEEEAVR LFIEWLKNGG PSSGAPPPS-NH$_2$ | 66 |
| HR64 | HdAEGTFTSDL SKQNleEEEAVR LFIEWLKNGG PSSGAPPPC-NH$_2$ | 67 |
| HR65 | HdAEGTFTSDL SKQNleEEEAVR LFIEWLKNGG PSSGAPPPCC-NH$_2$ | 68 |
| HR66 | HdAEGTFTSDL SKQNleEEEAVR LFIEWLKNGG PSSGAPPPhC-NH$_2$ | 69 |
| HR67 | HdAEGTFTSDL SKQNleEEEAVR LFIEWLKNGG PSSGAPPPhChC-NH$_2$ | 70 |
| HR68 | HdAEGTFTSDL SKQNleEEEAVR LFIEWLKNGG PSSGAPPPK*-NH$_2$ | 71 |

TABLE 7-continued

The amino acid sequences of the said long-lasting exendins of the present invention were given.

| Series Number | Sequences | SEQ ID NO |
|---|---|---|
| HR69 | HdAEGTFTSDL SKQNleEEEAVR LFIEWLKNGG PSSGAPPPK*K*-NH$_2$ | 72 |
| HR70 | HdAEGTFTSDL SKQMEEEAVR LFIEWLKQGG PSSGAPPPS | 73 |
| HR71 | HdAEGTFTSDL SKQMEEEAVR LFIEWLKQGG PSSGAPPPC | 74 |
| HR72 | HdAEGTFTSDL SKQMEEEAVR LFIEWLKQGG PSSGAPPPCC | 75 |
| HR73 | HdAEGTFTSDL SKQMEEEAVR LFIEWLKQGG PSSGAPPPhC | 76 |
| HR74 | HdAEGTFTSDL SKQMEEEAVR LFIEWLKQGG PSSGAPPPhChC | 77 |
| HR75 | HdAEGTFTSDL SKQMEEEAVR LFIEWLKQGG PSSGAPPPK* | 78 |
| HR76 | HdAEGTFTSDL SKQMEEEAVR LFIEWLKQGG PSSGAPPPK*K* | 79 |
| HR77 | HdAEGTFTSDL SKQMEEEAVR LFIEWLKQGG PSSGAPPPS-NH$_2$ | 80 |
| HR78 | HdAEGTFTSDL SKQMEEEAVR LFIEWLKQGG PSSGAPPPC-NH$_2$ | 81 |
| HR79 | HdAEGTFTSDL SKQMEEEAVR LFIEWLKQGG PSSGAPPPCC-NH$_2$ | 82 |
| HR80 | HdAEGTFTSDL SKQMEEEAVR LFIEWLKQGG PSSGAPPPhC-NH$_2$ | 83 |
| HR81 | HdAEGTFTSDL SKQMEEEAVR LFIEWLKQGG PSSGAPPPhChC-NH$_2$ | 84 |
| HR82 | HdAEGTFTSDL SKQMEEEAVR LFIEWLKQGG PSSGAPPPK*-NH$_2$ | 85 |
| HR83 | HdAEGTFTSDL SKQMEEEAVR LFIEWLKQGG PSSGAPPPK*K*-NH$_2$ | 86 |
| HR84 | HdAEGTFTSDL SKQNleEEEAVR LFIEWLKQGG PSSGAPPPS | 87 |
| HR85 | HdAEGTFTSDL SKQNleEEEAVR LFIEWLKQGG PSSGAPPPC | 88 |
| HR86 | HdAEGTFTSDL SKQNleEEEAVR LFIEWLKQGG PSSGAPPPCC | 89 |
| HR87 | HdAEGTFTSDL SKQNleEEEAVR LFIEWLKQGG PSSGAPPPhC | 90 |
| HR88 | HdAEGTFTSDL SKQNleEEEAVR LFIEWLKQGG PSSGAPPPhChC | 91 |
| HR89 | HdAEGTFTSDL SKQNleEEEAVR LFIEWLKQGG PSSGAPPPK* | 92 |
| HR90 | HdAEGTFTSDL SKQNleEEEAVR LFIEWLKQGG PSSGAPPPK*K* | 93 |
| HR91 | HdAEGTFTSDL SKQNleEEEAVR LFIEWLKQGG PSSGAPPPS-NH$_2$ | 94 |
| HR92 | HdAEGTFTSDL SKQNleEEEAVR LFIEWLKQGG PSSGAPPPC-NH$_2$ | 95 |
| HR93 | HdAEGTFTSDL SKQNleEEEAVR LFIEWLKQGG PSSGAPPPCC-NH$_2$ | 96 |
| HR94 | HdAEGTFTSDL SKQNleEEEAVR LFIEWLKQGG PSSGAPPPhChC-NH$_2$ | 97 |
| HR95 | HdAEGTFTSDL SKQNleEEEAVR LFIEWLKQGG PSSGAPPPK*-NH$_2$ | 98 |
| HR96 | HdAEGTFTSDL SKQNleEEEAVR LFIEWLKQGG PSSGAPPPK*K*-NH$_2$ | 99 |
| HR97 | HdAEGTFTSDL SKQNleEEEAVR LFIEWLQKGG PSSGAPPPS | 100 |
| HR98 | HdAEGTFTSDL SKQNleEEEAVR LFIEWLQKGG PSSGAPPPC | 101 |
| HR99 | HdAEGTFTSDL SKQNleEEEAVR LFIEWLQKGG PSSGAPPPCC | 102 |
| HR100 | HdAEGTFTSDL SKQNleEEEAVR LFIEWLQKGG PSSGAPPPhC | 103 |
| HR101 | HdAEGTFTSDL SKQNleEEEAVR LFIEWLQKGG PSSGAPPPhChC | 104 |
| HR102 | HdAEGTFTSDL SKQNleEEEAVR LFIEWLQKGG PSSGAPPPK* | 105 |
| HR103 | HdAEGTFTSDL SKQNleEEEAVR LFIEWLQKGG PSSGAPPPK*K* | 106 |
| HR104 | HdAEGTFTSDL SKQNleEEEAVR LFIEWLQKGG PSSGAPPPS-NH$_2$ | 107 |
| HR105 | HdAEGTFTSDL SKQNleEEEAVR LFIEWLQKGG PSSGAPPPC-NH$_2$ | 108 |

TABLE 7-continued

The amino acid sequences of the said long-lasting exendins of the present invention were given.

| Series Number | Sequences | SEQ ID NO |
|---|---|---|
| HR106 | HdAEGTFTSDL SKQNleEEEAVR LFIEWLQKGG PSSGAPPPCC-NH$_2$ | 109 |
| HR107 | HdAEGTFTSDL SKQNleEEEAVR LFIEWLQKGG PSSGAPPPhC-NH$_2$ | 110 |
| HR108 | HdAEGTFTSDL SKQNleEEEAVR LFIEWLQKGG PSSGAPPPhChC-NH$_2$ | 111 |
| HR109 | HdAEGTFTSDL SKQNleEEEAVR LFIEWLQKGG PSSGAPPPK*-NH$_2$ | 112 |
| HR110 | HdAEGTFTSDL SKQNleEEEAVR LFIEWLQKGG PSSGAPPPK*K*-NH$_2$ | 113 |
| HR111 | HdAEGTFTSDL SKQMEEEAVR LFIEWLVKGG PSSGAPPPS | 114 |
| HR112 | HdAEGTFTSDL SKQMEEEAVR LFIEWLVKGG PSSGAPPPC | 115 |
| HR113 | HdAEGTFTSDL SKQMEEEAVR LFIEWLVKGG PSSGAPPPCC | 116 |
| HR114 | HdAEGTFTSDL SKQMEEEAVR LFIEWLVKGG PSSGAPPPhC | 117 |
| HR115 | HdAEGTFTSDL SKQMEEEAVR LFIEWLVKGG PSSGAPPPhChC | 118 |
| HR116 | HdAEGTFTSDL SKQMEEEAVR LFIEWLVKGG PSSGAPPPK* | 119 |
| HR117 | HdAEGTFTSDL SKQMEEEAVR LFIEWLVKGG PSSGAPPPK*K* | 120 |
| HR118 | HdAEGTFTSDL SKQMEEEAVR LFIEWLVKGG PSSGAPPPS-NH$_2$ | 121 |
| HR119 | HdAEGTFTSDL SKQMEEEAVR LFIEWLVKGG PSSGAPPPC-NH$_2$ | 122 |
| HR120 | HdAEGTFTSDL SKQMEEEAVR LFIEWLVKGG PSSGAPPPCC-NH$_2$ | 123 |
| HR121 | HdAEGTFTSDL SKQMEEEAVR LFIEWLVKGG PSSGAPPPhC-NH$_2$ | 124 |
| HR122 | HdAEGTFTSDL SKQMEEEAVR LFIEWLVKGG PSSGAPPPhChC-NH$_2$ | 125 |
| HR123 | HdAEGTFTSDL SKQMEEEAVR LFIEWLVKGG PSSGAPPPK*-NH$_2$ | 126 |
| HR124 | HdAEGTFTSDL SKQMEEEAVR LFIEWLVKGG PSSGAPPPK*K*-NH$_2$ | 127 |
| HR125 | HdAEGTFTSDL SKQNleEEEAVR LFIEWLVKGG PSSGAPPPS | 128 |
| HR126 | HdAEGTFTSDL SKQNleEEEAVR LFIEWLVKGG PSSGAPPPC | 129 |
| HR127 | HdAEGTFTSDL SKQNleEEEAVR LFIEWLVKGG PSSGAPPPCC | 130 |
| HR128 | HdAEGTFTSDL SKQNleEEEAVR LFIEWLVKGG PSSGAPPPhC | 131 |
| HR129 | HdAEGTFTSDL SKQNleEEEAVR LFIEWLVKGG PSSGAPPPhChC | 132 |
| HR130 | HdAEGTFTSDL SKQNleEEEAVR LFIEWLVKGG PSSGAPPPK* | 133 |
| HR131 | HdAEGTFTSDL SKQNleEEEAVR LFIEWLVKGG PSSGAPPPK*K* | 134 |
| HR132 | HdAEGTFTSDL SKQNleEEEAVR LFIEWLVKGG PSSGAPPPS-NH$_2$ | 135 |
| HR133 | HdAEGTFTSDL SKQNleEEEAVR LFIEWLVKGG PSSGAPPPC-NH$_2$ | 136 |
| HR134 | HdAEGTFTSDL SKQNleEEEAVR LFIEWLVKGG PSSGAPPPCC-NH$_2$ | 137 |
| HR135 | HdAEGTFTSDL SKQNleEEEAVR LFIEWLVKGG PSSGAPPPhC-NH$_2$ | 138 |
| HR136 | HdAEGTFTSDL SKQNleEEEAVR LFIEWLVKGG PSSGAPPPhChC-NH$_2$ | 139 |
| HR137 | HdAEGTFTSDL SKQNleEEEAVR LFIEWLVKGG PSSGAPPPK*-NH$_2$ | 140 |
| HR138 | HdAEGTFTSDL SKQNleEEEAVR LFIEWLVKGG PSSGAPPPK*K*-NH$_2$ | 141 |

In table 7, C, hC, K* are the modification sites for pegylation. C is cysteine, hC is homocysteine and K* is lysine with a modified side-chain, such as the mercaptopropionic acid on the amino group of the side chain of lysine. CC, hChC or K*K* in the sequence represent two modification sites for pegylation. Nle is norleucine, dAlea is D-alanine, —NH$_2$ is an amide at the C-terminal.

The invention claimed is:

1. A modified exendin selected from a peptide that comprises any one of the amino acid sequences of SEQ ID Nos. 88, 89, 95 and 96.

2. A modified exendin or pharmaceutically acceptable salt thereof that comprises the amino acid sequence of SEQ ID No. 95 and polyethylene glycol (PEG) wherein the PEG has a molecular weight (MW) between 20,000 and 60,000 daltons.

3. The modified exendin of claim 2, wherein the MW of said PEG is 40,000 dalton.

4. The modified exendin of claim 3, wherein the modification is obtained by connecting the polyethylene glycol and the regiospecific group at the carboxyl terminal end of the peptide.

5. A method for treatment of type 2 diabetes, comprising administration of an effective dosage of a modified exendin or pharmaceutically acceptable salt thereof that comprises the amino acid sequence of SEQ ID No. 95 and polyethylene glycol (PEG) wherein the PEG has a molecular weight (MW) between 20,000 and 60,000 daltons to a patient in need thereof.

6. The method of claim 5, wherein the MW of said PEG is 40,000 dalton.

7. The method of claim 6, wherein the modification is obtained by connecting the polyethylene glycol and the regiospecific group at the carboxyl terminal end of the peptide.

8. A method for the reduction of blood glucose in a mammal comprising administration of an effective dosage of a modified exendin or a pharmaceutically acceptable salt thereof, to the mammal, wherein the modified exendin comprises the amino acid sequence of SEQ ID No. 95 and polyethylene glycol (PEG), and wherein the PEG has a molecular weight (MW) between 20,000 and 60,000 daltons.

9. The method of claim 8, wherein the PEG has a molecular weight (MW) of 40,000 dalton.

10. The method of claim 9, wherein the modification is obtained by connecting the polyethylene glycol and the regiospecific group at the carboxyl terminal end of the peptide.

11. A method for preparation of modified exendin or a pharmaceutically acceptable salt thereof, which comprises the amino acid sequence of SEQ ID No. 95 and polyethylene glycol (PEG) wherein the PEG has a molecular weight (MW) between 20,000 and 60,000 daltons, comprising solid phase and liquid-phase synthesis, reverse-phase high performance liquid chromatography, ion-exchange and gel filtration for purification or lyophilization.

12. The method of claim 11 wherein the PEG has a molecular weight (MW) of 40,000 dalton.

13. The method of claim 12, wherein the modification is obtained by connecting the polyethylene glycol and the regiospecific group at the carboxyl terminal end of the peptide.

* * * * *

SEQUENCE LISTING

<160> NUMBER OF SEQ ID NOS: 141

<210> SEQ ID NO 1
<211> LENGTH: 30
<212> TYPE: PRT
<213> ORGANISM: Artificial sequence
<220> FEATURE:
<223> OTHER INFORMATION: synthesized GLP-1 (7-36)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 31
<212> TYPE: PRT
<213> ORGANISM: Artificial sequence
<220> FEATURE:
<223> OTHER INFORMATION: synthesized GLP-1 (7-37)

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 39
<212> TYPE: PRT
<213> ORGANISM: Artificial sequence
<220> FEATURE:
<223> OTHER INFORMATION: synthesized Exendin-4

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial sequence
<220> FEATURE:
<223> OTHER INFORMATION: synthesized HR1

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial sequence
<220> FEATURE:

<223> OTHER INFORMATION: synthesized HR2

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 6
<211> LENGTH: 40
<212> TYPE: PRT
<213> ORGANISM: Artificial sequence
<220> FEATURE:
<223> OTHER INFORMATION: synthesized HR3

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 7
<211> LENGTH: 39
<212> TYPE: PRT
<213> ORGANISM: Artificial sequence
<220> FEATURE:
<223> OTHER INFORMATION: synthesized HR4

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 8
<211> LENGTH: 40
<212> TYPE: PRT
<213> ORGANISM: Artificial sequence
<220> FEATURE:
<223> OTHER INFORMATION: synthesized HR5

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 9
<211> LENGTH: 39
<212> TYPE: PRT
<213> ORGANISM: Artificial sequence
<220> FEATURE:
<223> OTHER INFORMATION: synthesized HR6

<400> SEQUENCE: 9

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Ser Gly Ala Pro Pro Lys
        35

<210> SEQ ID NO 10
<211> LENGTH: 40
<212> TYPE: PRT
<213> ORGANISM: Artificial sequence
<220> FEATURE:
<223> OTHER INFORMATION: synthesized HR7

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Lys
        35              40

<210> SEQ ID NO 11
<211> LENGTH: 39
<212> TYPE: PRT
<213> ORGANISM: Artificial sequence
<220> FEATURE:
<223> OTHER INFORMATION: synthesized HR8

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 12
<211> LENGTH: 40
<212> TYPE: PRT
<213> ORGANISM: Artificial sequence
<220> FEATURE:
<223> OTHER INFORMATION: synthesized HR9

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35              40

<210> SEQ ID NO 13
<211> LENGTH: 39
<212> TYPE: PRT
<213> ORGANISM: Artificial sequence
<220> FEATURE:
<223> OTHER INFORMATION: synthesized HR10

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser

```
            20                  25                  30

Ser Gly Ala Pro Pro Cys
        35

<210> SEQ ID NO 14
<211> LENGTH: 40
<212> TYPE: PRT
<213> ORGANISM: Artificial sequence
<220> FEATURE:
<223> OTHER INFORMATION: synthesized HR11

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 15
<211> LENGTH: 39
<212> TYPE: PRT
<213> ORGANISM: Artificial sequence
<220> FEATURE:
<223> OTHER INFORMATION: synthesized HR12

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys
        35

<210> SEQ ID NO 16
<211> LENGTH: 40
<212> TYPE: PRT
<213> ORGANISM: Artificial sequence
<220> FEATURE:
<223> OTHER INFORMATION: synthesized HR13

<400> SEQUENCE: 16

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys Lys
        35                  40

<210> SEQ ID NO 17
<211> LENGTH: 39
<212> TYPE: PRT
<213> ORGANISM: Artificial sequence
<220> FEATURE:
<223> OTHER INFORMATION: synthesized HR14

<400> SEQUENCE: 17

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

```
<210> SEQ ID NO 18
<211> LENGTH: 39
<212> TYPE: PRT
<213> ORGANISM: Artificial sequence
<220> FEATURE:
<223> OTHER INFORMATION: synthesized HR15

<400> SEQUENCE: 18

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 19
<211> LENGTH: 40
<212> TYPE: PRT
<213> ORGANISM: Artificial sequence
<220> FEATURE:
<223> OTHER INFORMATION: synthesized HR16

<400> SEQUENCE: 19

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 20
<211> LENGTH: 39
<212> TYPE: PRT
<213> ORGANISM: Artificial sequence
<220> FEATURE:
<223> OTHER INFORMATION: synthesized HR17

<400> SEQUENCE: 20

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 21
<211> LENGTH: 40
<212> TYPE: PRT
<213> ORGANISM: Artificial sequence
<220> FEATURE:
<223> OTHER INFORMATION: synthesized HR18

<400> SEQUENCE: 21

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 22
<211> LENGTH: 39
```

```
<212> TYPE: PRT
<213> ORGANISM: Artificial sequence
<220> FEATURE:
<223> OTHER INFORMATION: synthesized HR19

<400> SEQUENCE: 22

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys
        35

<210> SEQ ID NO 23
<211> LENGTH: 40
<212> TYPE: PRT
<213> ORGANISM: Artificial sequence
<220> FEATURE:
<223> OTHER INFORMATION: synthesized HR20

<400> SEQUENCE: 23

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys Lys
        35                  40

<210> SEQ ID NO 24
<211> LENGTH: 39
<212> TYPE: PRT
<213> ORGANISM: Artificial sequence
<220> FEATURE:
<223> OTHER INFORMATION: synthesized HR21

<400> SEQUENCE: 24

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial sequence
<220> FEATURE:
<223> OTHER INFORMATION: synthesized HR22

<400> SEQUENCE: 25

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 26
<211> LENGTH: 40
<212> TYPE: PRT
<213> ORGANISM: Artificial sequence
<220> FEATURE:
<223> OTHER INFORMATION: synthesized HR23
```

```
<400> SEQUENCE: 26

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 27
<211> LENGTH: 39
<212> TYPE: PRT
<213> ORGANISM: Artificial sequence
<220> FEATURE:
<223> OTHER INFORMATION: synthesized HR24

<400> SEQUENCE: 27

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 28
<211> LENGTH: 40
<212> TYPE: PRT
<213> ORGANISM: Artificial sequence
<220> FEATURE:
<223> OTHER INFORMATION: synthesized HR25

<400> SEQUENCE: 28

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 29
<211> LENGTH: 39
<212> TYPE: PRT
<213> ORGANISM: Artificial sequence
<220> FEATURE:
<223> OTHER INFORMATION: synthesized HR26

<400> SEQUENCE: 29

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys
        35

<210> SEQ ID NO 30
<211> LENGTH: 40
<212> TYPE: PRT
<213> ORGANISM: Artificial sequence
<220> FEATURE:
<223> OTHER INFORMATION: synthesized HR27

<400> SEQUENCE: 30

His Ala Glu Gly Thr Phe Thr Ser Asp Leu Ser Lys Gln Met Glu Glu
```

```
                 1               5                  10                 15
Glu Ala Val Arg Leu Phe Ile Glu Trp Leu Lys Asn Gly Gly Pro Ser
                20                 25                 30

Ser Gly Ala Pro Pro Lys Lys
        35                 40

<210> SEQ ID NO 31
<211> LENGTH: 39
<212> TYPE: PRT
<213> ORGANISM: Artificial sequence
<220> FEATURE:
<223> OTHER INFORMATION: synthesized HR28
<220> FEATURE:
<221> NAME/KEY: SITE
<222> LOCATION: (14)..(14)
<223> OTHER INFORMATION: Xaa is Nle = norleucine

<400> SEQUENCE: 31

His Gly Glu Gly Thr Phe Thr Ser Asp Leu Ser Lys Gln Xaa Glu Glu
1               5                  10                 15

Glu Ala Val Arg Leu Phe Ile Glu Trp Leu Lys Asn Gly Gly Pro Ser
                20                 25                 30

Ser Gly Ala Pro Pro Pro Ser
        35

<210> SEQ ID NO 32
<211> LENGTH: 39
<212> TYPE: PRT
<213> ORGANISM: Artificial sequence
<220> FEATURE:
<223> OTHER INFORMATION: synthesized HR29
<220> FEATURE:
<221> NAME/KEY: SITE
<222> LOCATION: (14)..(14)
<223> OTHER INFORMATION: Xaa is Nle = norleucine

<400> SEQUENCE: 32

His Gly Glu Gly Thr Phe Thr Ser Asp Leu Ser Lys Gln Xaa Glu Glu
1               5                  10                 15

Glu Ala Val Arg Leu Phe Ile Glu Trp Leu Lys Asn Gly Gly Pro Ser
                20                 25                 30

Ser Gly Ala Pro Pro Pro Cys
        35

<210> SEQ ID NO 33
<211> LENGTH: 40
<212> TYPE: PRT
<213> ORGANISM: Artificial sequence
<220> FEATURE:
<223> OTHER INFORMATION: synthesized HR30
<220> FEATURE:
<221> NAME/KEY: SITE
<222> LOCATION: (14)..(14)
<223> OTHER INFORMATION: Xaa is Nle = norleucine

<400> SEQUENCE: 33

His Gly Glu Gly Thr Phe Thr Ser Asp Leu Ser Lys Gln Xaa Glu Glu
1               5                  10                 15

Glu Ala Val Arg Leu Phe Ile Glu Trp Leu Lys Asn Gly Gly Pro Ser
                20                 25                 30

Ser Gly Ala Pro Pro Pro Cys Cys
        35                 40

<210> SEQ ID NO 34
<211> LENGTH: 39
```

```
<212> TYPE: PRT
<213> ORGANISM: Artificial sequence
<220> FEATURE:
<223> OTHER INFORMATION: synthesized HR31
<220> FEATURE:
<221> NAME/KEY: SITE
<222> LOCATION: (14)..(14)
<223> OTHER INFORMATION: Xaa is Nle = norleucine

<400> SEQUENCE: 34

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 35
<211> LENGTH: 40
<212> TYPE: PRT
<213> ORGANISM: Artificial sequence
<220> FEATURE:
<223> OTHER INFORMATION: synthesized HR32
<220> FEATURE:
<221> NAME/KEY: SITE
<222> LOCATION: (14)..(14)
<223> OTHER INFORMATION: Xaa is Nle = norleucine

<400> SEQUENCE: 35

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 36
<211> LENGTH: 39
<212> TYPE: PRT
<213> ORGANISM: Artificial sequence
<220> FEATURE:
<223> OTHER INFORMATION: synthesized HR33
<220> FEATURE:
<221> NAME/KEY: SITE
<222> LOCATION: (14)..(14)
<223> OTHER INFORMATION: Xaa is Nle = norleucine

<400> SEQUENCE: 36

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys
        35

<210> SEQ ID NO 37
<211> LENGTH: 40
<212> TYPE: PRT
<213> ORGANISM: Artificial sequence
<220> FEATURE:
<223> OTHER INFORMATION: synthesized HR34
<220> FEATURE:
<221> NAME/KEY: SITE
<222> LOCATION: (14)..(14)
<223> OTHER INFORMATION: Xaa is Nle = norleucine

<400> SEQUENCE: 37
```

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Lys
        35                  40

<210> SEQ ID NO 38
<211> LENGTH: 39
<212> TYPE: PRT
<213> ORGANISM: Artificial sequence
<220> FEATURE:
<223> OTHER INFORMATION: synthesized HR35
<220> FEATURE:
<221> NAME/KEY: SITE
<222> LOCATION: (14)..(14)
<223> OTHER INFORMATION: Xaa is Nle = norleucine

<400> SEQUENCE: 38

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 39
<211> LENGTH: 39
<212> TYPE: PRT
<213> ORGANISM: Artificial sequence
<220> FEATURE:
<223> OTHER INFORMATION: synthesized HR36
<220> FEATURE:
<221> NAME/KEY: SITE
<222> LOCATION: (14)..(14)
<223> OTHER INFORMATION: Xaa is Nle = norleucine

<400> SEQUENCE: 39

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Cys
        35

<210> SEQ ID NO 40
<211> LENGTH: 40
<212> TYPE: PRT
<213> ORGANISM: Artificial sequence
<220> FEATURE:
<223> OTHER INFORMATION: synthesized HR37
<220> FEATURE:
<221> NAME/KEY: SITE
<222> LOCATION: (14)..(14)
<223> OTHER INFORMATION: Xaa is Nle = norleucine

<400> SEQUENCE: 40

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Cys Cys
        35                  40

<210> SEQ ID NO 41

```
<211> LENGTH: 39
<212> TYPE: PRT
<213> ORGANISM: Artificial sequence
<220> FEATURE:
<223> OTHER INFORMATION: synthesized HR38
<220> FEATURE:
<221> NAME/KEY: SITE
<222> LOCATION: (14)..(14)
<223> OTHER INFORMATION: Xaa is Nle = norleucine

<400> SEQUENCE: 41

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 42
<211> LENGTH: 40
<212> TYPE: PRT
<213> ORGANISM: Artificial sequence
<220> FEATURE:
<223> OTHER INFORMATION: synthesized HR39
<220> FEATURE:
<221> NAME/KEY: SITE
<222> LOCATION: (14)..(14)
<223> OTHER INFORMATION: Xaa is Nle = norleucine

<400> SEQUENCE: 42

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 43
<211> LENGTH: 39
<212> TYPE: PRT
<213> ORGANISM: Artificial sequence
<220> FEATURE:
<223> OTHER INFORMATION: synthesized HR40
<220> FEATURE:
<221> NAME/KEY: SITE
<222> LOCATION: (14)..(14)
<223> OTHER INFORMATION: Xaa is Nle = norleucine

<400> SEQUENCE: 43

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys
        35

<210> SEQ ID NO 44
<211> LENGTH: 40
<212> TYPE: PRT
<213> ORGANISM: Artificial sequence
<220> FEATURE:
<223> OTHER INFORMATION: synthesized HR41
<220> FEATURE:
<221> NAME/KEY: SITE
<222> LOCATION: (14)..(14)
<223> OTHER INFORMATION: Xaa is Nle = norleucine

<400> SEQUENCE: 44
```

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Lys
        35              40

<210> SEQ ID NO 45
<211> LENGTH: 39
<212> TYPE: PRT
<213> ORGANISM: Artificial sequence
<220> FEATURE:
<223> OTHER INFORMATION: synthesized HR42

<400> SEQUENCE: 45

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial sequence
<220> FEATURE:
<223> OTHER INFORMATION: synthesized HR43

<400> SEQUENCE: 46

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys
        35

<210> SEQ ID NO 47
<211> LENGTH: 40
<212> TYPE: PRT
<213> ORGANISM: Artificial sequence
<220> FEATURE:
<223> OTHER INFORMATION: synthesized HR44

<400> SEQUENCE: 47

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys Cys
        35              40

<210> SEQ ID NO 48
<211> LENGTH: 39
<212> TYPE: PRT
<213> ORGANISM: Artificial sequence
<220> FEATURE:
<223> OTHER INFORMATION: synthesized HR45

<400> SEQUENCE: 48

His Gly Glu Gly Thr Phe Thr Ser Asp Leu Ser Lys Gln Met Glu Glu
1               5                   10                  15

-continued

Glu Ala Val Arg Leu Phe Ile Glu Trp Leu Lys Gln Gly Gly Pro Ser
            20                  25                  30

Ser Gly Ala Pro Pro Cys
            35

<210> SEQ ID NO 49
<211> LENGTH: 39
<212> TYPE: PRT
<213> ORGANISM: Artificial sequence
<220> FEATURE:
<223> OTHER INFORMATION: synthesized HR46

<400> SEQUENCE: 49

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Cys Cys
            35

<210> SEQ ID NO 50
<211> LENGTH: 39
<212> TYPE: PRT
<213> ORGANISM: Artificial sequence
<220> FEATURE:
<223> OTHER INFORMATION: synthesized HR47

<400> SEQUENCE: 50

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Lys
            35

<210> SEQ ID NO 51
<211> LENGTH: 40
<212> TYPE: PRT
<213> ORGANISM: Artificial sequence
<220> FEATURE:
<223> OTHER INFORMATION: synthesized HR48

<400> SEQUENCE: 51

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Lys Lys
            35                  40

<210> SEQ ID NO 52
<211> LENGTH: 39
<212> TYPE: PRT
<213> ORGANISM: Artificial sequence
<220> FEATURE:
<223> OTHER INFORMATION: synthesized HR49

<400> SEQUENCE: 52

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Ser

-continued

<210> SEQ ID NO 53
<211> LENGTH: 39
<212> TYPE: PRT
<213> ORGANISM: Artificial sequence
<220> FEATURE:
<223> OTHER INFORMATION: synthesized HR50

<400> SEQUENCE: 53

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys
        35

<210> SEQ ID NO 54
<211> LENGTH: 40
<212> TYPE: PRT
<213> ORGANISM: Artificial sequence
<220> FEATURE:
<223> OTHER INFORMATION: synthesized HR51

<400> SEQUENCE: 54

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys Cys
        35                  40

<210> SEQ ID NO 55
<211> LENGTH: 39
<212> TYPE: PRT
<213> ORGANISM: Artificial sequence
<220> FEATURE:
<223> OTHER INFORMATION: synthesized HR52

<400> SEQUENCE: 55

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys
        35

<210> SEQ ID NO 56
<211> LENGTH: 40
<212> TYPE: PRT
<213> ORGANISM: Artificial sequence
<220> FEATURE:
<223> OTHER INFORMATION: synthesized HR53

<400> SEQUENCE: 56

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys Cys
        35                  40

<210> SEQ ID NO 57

```
<211> LENGTH: 39
<212> TYPE: PRT
<213> ORGANISM: Artificial sequence
<220> FEATURE:
<223> OTHER INFORMATION: synthesized HR54

<400> SEQUENCE: 57

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Lys
        35

<210> SEQ ID NO 58
<211> LENGTH: 40
<212> TYPE: PRT
<213> ORGANISM: Artificial sequence
<220> FEATURE:
<223> OTHER INFORMATION: synthesized HR55

<400> SEQUENCE: 58

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Lys Lys
        35                  40

<210> SEQ ID NO 59
<211> LENGTH: 39
<212> TYPE: PRT
<213> ORGANISM: Artificial sequence
<220> FEATURE:
<223> OTHER INFORMATION: synthesized HR56
<220> FEATURE:
<221> NAME/KEY: SITE
<222> LOCATION: (14)..(14)
<223> OTHER INFORMATION: Xaa is Nle = norleucine

<400> SEQUENCE: 59

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 60
<211> LENGTH: 39
<212> TYPE: PRT
<213> ORGANISM: Artificial sequence
<220> FEATURE:
<223> OTHER INFORMATION: synthesized HR57
<220> FEATURE:
<221> NAME/KEY: SITE
<222> LOCATION: (14)..(14)
<223> OTHER INFORMATION: Xaa is Nle = norleucine

<400> SEQUENCE: 60

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
```

-continued

```
<210> SEQ ID NO 61
<211> LENGTH: 40
<212> TYPE: PRT
<213> ORGANISM: Artificial sequence
<220> FEATURE:
<223> OTHER INFORMATION: synthesized HR58
<220> FEATURE:
<221> NAME/KEY: SITE
<222> LOCATION: (14)..(14)
<223> OTHER INFORMATION: Xaa is Nle = norleucine

<400> SEQUENCE: 61

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 62
<211> LENGTH: 39
<212> TYPE: PRT
<213> ORGANISM: Artificial sequence
<220> FEATURE:
<223> OTHER INFORMATION: synthesized HR59
<220> FEATURE:
<221> NAME/KEY: SITE
<222> LOCATION: (14)..(14)
<223> OTHER INFORMATION: Xaa is Nle = norleucine

<400> SEQUENCE: 62

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 63
<211> LENGTH: 40
<212> TYPE: PRT
<213> ORGANISM: Artificial sequence
<220> FEATURE:
<223> OTHER INFORMATION: synthesized HR60
<220> FEATURE:
<221> NAME/KEY: SITE
<222> LOCATION: (14)..(14)
<223> OTHER INFORMATION: Xaa is Nle = norleucine

<400> SEQUENCE: 63

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 64
<211> LENGTH: 39
<212> TYPE: PRT
<213> ORGANISM: Artificial sequence
<220> FEATURE:
<223> OTHER INFORMATION: synthesized HR61
<220> FEATURE:
<221> NAME/KEY: SITE
```

```
<222> LOCATION: (14)..(14)
<223> OTHER INFORMATION: Xaa is Nle = norleucine

<400> SEQUENCE: 64

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys
        35

<210> SEQ ID NO 65
<211> LENGTH: 40
<212> TYPE: PRT
<213> ORGANISM: Artificial sequence
<220> FEATURE:
<223> OTHER INFORMATION: synthesized HR62
<220> FEATURE:
<221> NAME/KEY: SITE
<222> LOCATION: (14)..(14)
<223> OTHER INFORMATION: Xaa is Nle = norleucine

<400> SEQUENCE: 65

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys Lys
        35                  40

<210> SEQ ID NO 66
<211> LENGTH: 39
<212> TYPE: PRT
<213> ORGANISM: Artificial sequence
<220> FEATURE:
<223> OTHER INFORMATION: synthesized HR63
<220> FEATURE:
<221> NAME/KEY: SITE
<222> LOCATION: (14)..(14)
<223> OTHER INFORMATION: Xaa is Nle = norleucine

<400> SEQUENCE: 66

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 67
<211> LENGTH: 39
<212> TYPE: PRT
<213> ORGANISM: Artificial sequence
<220> FEATURE:
<223> OTHER INFORMATION: synthesized HR64
<220> FEATURE:
<221> NAME/KEY: SITE
<222> LOCATION: (14)..(14)
<223> OTHER INFORMATION: Xaa is Nle = norleucine

<400> SEQUENCE: 67

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30
```

Ser Gly Ala Pro Pro Pro Cys
        35

<210> SEQ ID NO 68
<211> LENGTH: 40
<212> TYPE: PRT
<213> ORGANISM: Artificial sequence
<220> FEATURE:
<223> OTHER INFORMATION: synthesized HR65
<220> FEATURE:
<221> NAME/KEY: SITE
<222> LOCATION: (14)..(14)
<223> OTHER INFORMATION: Xaa is Nle = norleucine

<400> SEQUENCE: 68

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 69
<211> LENGTH: 39
<212> TYPE: PRT
<213> ORGANISM: Artificial sequence
<220> FEATURE:
<223> OTHER INFORMATION: synthesized HR66
<220> FEATURE:
<221> NAME/KEY: SITE
<222> LOCATION: (14)..(14)
<223> OTHER INFORMATION: Xaa is Nle = norleucine

<400> SEQUENCE: 69

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys
        35

<210> SEQ ID NO 70
<211> LENGTH: 40
<212> TYPE: PRT
<213> ORGANISM: Artificial sequence
<220> FEATURE:
<223> OTHER INFORMATION: synthesized HR67
<220> FEATURE:
<221> NAME/KEY: SITE
<222> LOCATION: (14)..(14)
<223> OTHER INFORMATION: Xaa is Nle = norleucine

<400> SEQUENCE: 70

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Cys Cys
        35                  40

<210> SEQ ID NO 71
<211> LENGTH: 39
<212> TYPE: PRT
<213> ORGANISM: Artificial sequence
<220> FEATURE:
<223> OTHER INFORMATION: synthesized HR68
<220> FEATURE:

```
<221> NAME/KEY: SITE
<222> LOCATION: (14)..(14)
<223> OTHER INFORMATION: Xaa is Nle = norleucine

<400> SEQUENCE: 71

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys
        35

<210> SEQ ID NO 72
<211> LENGTH: 40
<212> TYPE: PRT
<213> ORGANISM: Artificial sequence
<220> FEATURE:
<223> OTHER INFORMATION: synthesized HR69
<220> FEATURE:
<221> NAME/KEY: SITE
<222> LOCATION: (14)..(14)
<223> OTHER INFORMATION: Xaa is Nle = norleucine

<400> SEQUENCE: 72

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Lys Lys
        35                  40

<210> SEQ ID NO 73
<211> LENGTH: 39
<212> TYPE: PRT
<213> ORGANISM: Artificial sequence
<220> FEATURE:
<223> OTHER INFORMATION: synthesized HR70

<400> SEQUENCE: 73

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Ser
        35

<210> SEQ ID NO 74
<211> LENGTH: 39
<212> TYPE: PRT
<213> ORGANISM: Artificial sequence
<220> FEATURE:
<223> OTHER INFORMATION: synthesized HR71

<400> SEQUENCE: 74

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys
        35

<210> SEQ ID NO 75
<211> LENGTH: 40
<212> TYPE: PRT
```

```
<213> ORGANISM: Artificial sequence
<220> FEATURE:
<223> OTHER INFORMATION: synthesized HR72

<400> SEQUENCE: 75

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys Cys
        35                  40

<210> SEQ ID NO 76
<211> LENGTH: 39
<212> TYPE: PRT
<213> ORGANISM: Artificial sequence
<220> FEATURE:
<223> OTHER INFORMATION: synthesized HR73

<400> SEQUENCE: 76

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys
        35

<210> SEQ ID NO 77
<211> LENGTH: 40
<212> TYPE: PRT
<213> ORGANISM: Artificial sequence
<220> FEATURE:
<223> OTHER INFORMATION: synthesized HR74

<400> SEQUENCE: 77

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys Cys
        35                  40

<210> SEQ ID NO 78
<211> LENGTH: 39
<212> TYPE: PRT
<213> ORGANISM: Artificial sequence
<220> FEATURE:
<223> OTHER INFORMATION: synthesized HR75

<400> SEQUENCE: 78

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Lys
        35

<210> SEQ ID NO 79
<211> LENGTH: 40
<212> TYPE: PRT
<213> ORGANISM: Artificial sequence
<220> FEATURE:
<223> OTHER INFORMATION: synthesized HR76
```

<400> SEQUENCE: 79

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Lys Lys
        35                  40

<210> SEQ ID NO 80
<211> LENGTH: 39
<212> TYPE: PRT
<213> ORGANISM: Artificial sequence
<220> FEATURE:
<223> OTHER INFORMATION: synthesized HR77

<400> SEQUENCE: 80

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Ser
        35

<210> SEQ ID NO 81
<211> LENGTH: 39
<212> TYPE: PRT
<213> ORGANISM: Artificial sequence
<220> FEATURE:
<223> OTHER INFORMATION: synthesized HR78

<400> SEQUENCE: 81

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Cys
        35

<210> SEQ ID NO 82
<211> LENGTH: 40
<212> TYPE: PRT
<213> ORGANISM: Artificial sequence
<220> FEATURE:
<223> OTHER INFORMATION: synthesized HR79

<400> SEQUENCE: 82

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Cys Cys
        35                  40

<210> SEQ ID NO 83
<211> LENGTH: 39
<212> TYPE: PRT
<213> ORGANISM: Artificial sequence
<220> FEATURE:
<223> OTHER INFORMATION: synthesized HR80

<400> SEQUENCE: 83

His Ala Glu Gly Thr Phe Thr Ser Asp Leu Ser Lys Gln Met Glu Glu
1               5                   10                  15

```
Glu Ala Val Arg Leu Phe Ile Glu Trp Leu Lys Gln Gly Gly Pro Ser
            20                  25                  30

Ser Gly Ala Pro Pro Cys
        35

<210> SEQ ID NO 84
<211> LENGTH: 40
<212> TYPE: PRT
<213> ORGANISM: Artificial sequence
<220> FEATURE:
<223> OTHER INFORMATION: synthesized HR81

<400> SEQUENCE: 84

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Cys Cys
        35                  40

<210> SEQ ID NO 85
<211> LENGTH: 39
<212> TYPE: PRT
<213> ORGANISM: Artificial sequence
<220> FEATURE:
<223> OTHER INFORMATION: synthesized HR82

<400> SEQUENCE: 85

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Lys
        35

<210> SEQ ID NO 86
<211> LENGTH: 40
<212> TYPE: PRT
<213> ORGANISM: Artificial sequence
<220> FEATURE:
<223> OTHER INFORMATION: synthesized HR83

<400> SEQUENCE: 86

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Lys Lys
        35                  40

<210> SEQ ID NO 87
<211> LENGTH: 39
<212> TYPE: PRT
<213> ORGANISM: Artificial sequence
<220> FEATURE:
<223> OTHER INFORMATION: synthesized HR84
<220> FEATURE:
<221> NAME/KEY: SITE
<222> LOCATION: (14)..(14)
<223> OTHER INFORMATION: Xaa is Nle = norleucine

<400> SEQUENCE: 87

His Ala Glu Gly Thr Phe Thr Ser Asp Leu Ser Lys Gln Xaa Glu Glu
1               5                   10                  15
```

```
Glu Ala Val Arg Leu Phe Ile Glu Trp Leu Lys Gln Gly Gly Pro Ser
            20                  25                  30

Ser Gly Ala Pro Pro Ser
        35

<210> SEQ ID NO 88
<211> LENGTH: 39
<212> TYPE: PRT
<213> ORGANISM: Artificial sequence
<220> FEATURE:
<223> OTHER INFORMATION: synthesized HR85
<220> FEATURE:
<221> NAME/KEY: SITE
<222> LOCATION: (14)..(14)
<223> OTHER INFORMATION: Xaa is Nle = norleucine

<400> SEQUENCE: 88

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Cys
        35

<210> SEQ ID NO 89
<211> LENGTH: 40
<212> TYPE: PRT
<213> ORGANISM: Artificial sequence
<220> FEATURE:
<223> OTHER INFORMATION: synthesized HR86
<220> FEATURE:
<221> NAME/KEY: SITE
<222> LOCATION: (14)..(14)
<223> OTHER INFORMATION: Xaa is Nle = norleucine

<400> SEQUENCE: 89

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Cys Cys
        35                  40

<210> SEQ ID NO 90
<211> LENGTH: 39
<212> TYPE: PRT
<213> ORGANISM: Artificial sequence
<220> FEATURE:
<223> OTHER INFORMATION: synthesized HR87
<220> FEATURE:
<221> NAME/KEY: SITE
<222> LOCATION: (14)..(14)
<223> OTHER INFORMATION: Xaa is Nle = norleucine

<400> SEQUENCE: 90

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Cys
        35

<210> SEQ ID NO 91
<211> LENGTH: 40
<212> TYPE: PRT
```

<213> ORGANISM: Artificial sequence
<220> FEATURE:
<223> OTHER INFORMATION: synthesized HR88
<220> FEATURE:
<221> NAME/KEY: SITE
<222> LOCATION: (14)..(14)
<223> OTHER INFORMATION: Xaa is Nle = norleucine

<400> SEQUENCE: 91

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys Cys
        35                  40

<210> SEQ ID NO 92
<211> LENGTH: 39
<212> TYPE: PRT
<213> ORGANISM: Artificial sequence
<220> FEATURE:
<223> OTHER INFORMATION: synthesized HR89
<220> FEATURE:
<221> NAME/KEY: SITE
<222> LOCATION: (14)..(14)
<223> OTHER INFORMATION: Xaa is Nle = norleucine

<400> SEQUENCE: 92

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Lys
        35

<210> SEQ ID NO 93
<211> LENGTH: 40
<212> TYPE: PRT
<213> ORGANISM: Artificial sequence
<220> FEATURE:
<223> OTHER INFORMATION: synthesized HR90
<220> FEATURE:
<221> NAME/KEY: SITE
<222> LOCATION: (14)..(14)
<223> OTHER INFORMATION: Xaa is Nle = norleucine

<400> SEQUENCE: 93

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Lys Lys
        35                  40

<210> SEQ ID NO 94
<211> LENGTH: 39
<212> TYPE: PRT
<213> ORGANISM: Artificial sequence
<220> FEATURE:
<223> OTHER INFORMATION: synthesized HR91
<220> FEATURE:
<221> NAME/KEY: SITE
<222> LOCATION: (14)..(14)
<223> OTHER INFORMATION: Xaa is Nle = norleucine

<400> SEQUENCE: 94

His Ala Glu Gly Thr Phe Thr Ser Asp Leu Ser Lys Gln Xaa Glu Glu

```
1               5                   10                  15
Glu Ala Val Arg Leu Phe Ile Glu Trp Leu Lys Gln Gly Gly Pro Ser
            20                  25                  30

Ser Gly Ala Pro Pro Ser
            35
```

<210> SEQ ID NO 95
<211> LENGTH: 39
<212> TYPE: PRT
<213> ORGANISM: Artificial sequence
<220> FEATURE:
<223> OTHER INFORMATION: synthesized HR92
<220> FEATURE:
<221> NAME/KEY: SITE
<222> LOCATION: (14)..(14)
<223> OTHER INFORMATION: Xaa is Nle = norleucine

<400> SEQUENCE: 95

```
His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Cys
            35
```

<210> SEQ ID NO 96
<211> LENGTH: 40
<212> TYPE: PRT
<213> ORGANISM: Artificial sequence
<220> FEATURE:
<223> OTHER INFORMATION: synthesized HR93
<220> FEATURE:
<221> NAME/KEY: SITE
<222> LOCATION: (14)..(14)
<223> OTHER INFORMATION: Xaa is Nle = norleucine

<400> SEQUENCE: 96

```
His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Cys Cys
            35                  40
```

<210> SEQ ID NO 97
<211> LENGTH: 40
<212> TYPE: PRT
<213> ORGANISM: Artificial sequence
<220> FEATURE:
<223> OTHER INFORMATION: synthesized HR94
<220> FEATURE:
<221> NAME/KEY: SITE
<222> LOCATION: (14)..(14)
<223> OTHER INFORMATION: Xaa is Nle = norleucine

<400> SEQUENCE: 97

```
His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Cys Cys
            35                  40
```

<210> SEQ ID NO 98
<211> LENGTH: 39

```
<212> TYPE: PRT
<213> ORGANISM: Artificial sequence
<220> FEATURE:
<223> OTHER INFORMATION: synthesized HR95
<220> FEATURE:
<221> NAME/KEY: SITE
<222> LOCATION: (14)..(14)
<223> OTHER INFORMATION: Xaa is Nle = norleucine

<400> SEQUENCE: 98

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Lys
        35

<210> SEQ ID NO 99
<211> LENGTH: 40
<212> TYPE: PRT
<213> ORGANISM: Artificial sequence
<220> FEATURE:
<223> OTHER INFORMATION: synthesized HR96
<220> FEATURE:
<221> NAME/KEY: SITE
<222> LOCATION: (14)..(14)
<223> OTHER INFORMATION: Xaa is Nle = norleucine

<400> SEQUENCE: 99

His Ala Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Lys Lys
        35                  40

<210> SEQ ID NO 100
<211> LENGTH: 39
<212> TYPE: PRT
<213> ORGANISM: Artificial sequence
<220> FEATURE:
<223> OTHER INFORMATION: synthesized HR97
<220> FEATURE:
<221> NAME/KEY: SITE
<222> LOCATION: (14)..(14)
<223> OTHER INFORMATION: Xaa is Nle = norleucine

<400> SEQUENCE: 100

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Ser
        35

<210> SEQ ID NO 101
<211> LENGTH: 39
<212> TYPE: PRT
<213> ORGANISM: Artificial sequence
<220> FEATURE:
<223> OTHER INFORMATION: synthesized HR98
<220> FEATURE:
<221> NAME/KEY: SITE
<222> LOCATION: (14)..(14)
<223> OTHER INFORMATION: Xaa is Nle = norleucine

<400> SEQUENCE: 101
```

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Cys
        35

<210> SEQ ID NO 102
<211> LENGTH: 40
<212> TYPE: PRT
<213> ORGANISM: Artificial sequence
<220> FEATURE:
<223> OTHER INFORMATION: synthesized HR99
<220> FEATURE:
<221> NAME/KEY: SITE
<222> LOCATION: (14)..(14)
<223> OTHER INFORMATION: Xaa is Nle = norleucine

<400> SEQUENCE: 102

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Cys Cys
        35                  40

<210> SEQ ID NO 103
<211> LENGTH: 39
<212> TYPE: PRT
<213> ORGANISM: Artificial sequence
<220> FEATURE:
<223> OTHER INFORMATION: synthesized HR100
<220> FEATURE:
<221> NAME/KEY: SITE
<222> LOCATION: (14)..(14)
<223> OTHER INFORMATION: Xaa is Nle = norleucine

<400> SEQUENCE: 103

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Cys
        35

<210> SEQ ID NO 104
<211> LENGTH: 40
<212> TYPE: PRT
<213> ORGANISM: Artificial sequence
<220> FEATURE:
<223> OTHER INFORMATION: synthesized HR101
<220> FEATURE:
<221> NAME/KEY: SITE
<222> LOCATION: (14)..(14)
<223> OTHER INFORMATION: Xaa is Nle = norleucine

<400> SEQUENCE: 104

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Cys Cys
        35                  40

<210> SEQ ID NO 105

```
<211> LENGTH: 39
<212> TYPE: PRT
<213> ORGANISM: Artificial sequence
<220> FEATURE:
<223> OTHER INFORMATION: synthesized HR102
<220> FEATURE:
<221> NAME/KEY: SITE
<222> LOCATION: (14)..(14)
<223> OTHER INFORMATION: Xaa is Nle = norleucine

<400> SEQUENCE: 105

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Lys
        35

<210> SEQ ID NO 106
<211> LENGTH: 40
<212> TYPE: PRT
<213> ORGANISM: Artificial sequence
<220> FEATURE:
<223> OTHER INFORMATION: synthesized HR103
<220> FEATURE:
<221> NAME/KEY: SITE
<222> LOCATION: (14)..(14)
<223> OTHER INFORMATION: Xaa is Nle = norleucine

<400> SEQUENCE: 106

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Lys Lys
        35                  40

<210> SEQ ID NO 107
<211> LENGTH: 39
<212> TYPE: PRT
<213> ORGANISM: Artificial sequence
<220> FEATURE:
<223> OTHER INFORMATION: synthesized HR104
<220> FEATURE:
<221> NAME/KEY: SITE
<222> LOCATION: (14)..(14)
<223> OTHER INFORMATION: Xaa is Nle = norleucine

<400> SEQUENCE: 107

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Ser
        35

<210> SEQ ID NO 108
<211> LENGTH: 39
<212> TYPE: PRT
<213> ORGANISM: Artificial sequence
<220> FEATURE:
<223> OTHER INFORMATION: synthesized HR105
<220> FEATURE:
<221> NAME/KEY: SITE
<222> LOCATION: (14)..(14)
<223> OTHER INFORMATION: Xaa is Nle = norleucine

<400> SEQUENCE: 108
```

-continued

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Cys
        35

<210> SEQ ID NO 109
<211> LENGTH: 40
<212> TYPE: PRT
<213> ORGANISM: Artificial sequence
<220> FEATURE:
<223> OTHER INFORMATION: synthesized HR106
<220> FEATURE:
<221> NAME/KEY: SITE
<222> LOCATION: (14)..(14)
<223> OTHER INFORMATION: Xaa is Nle = norleucine

<400> SEQUENCE: 109

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Cys Cys
        35                  40

<210> SEQ ID NO 110
<211> LENGTH: 39
<212> TYPE: PRT
<213> ORGANISM: Artificial sequence
<220> FEATURE:
<223> OTHER INFORMATION: synthesized HR107
<220> FEATURE:
<221> NAME/KEY: SITE
<222> LOCATION: (14)..(14)
<223> OTHER INFORMATION: Xaa is Nle = norleucine

<400> SEQUENCE: 110

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Cys
        35

<210> SEQ ID NO 111
<211> LENGTH: 40
<212> TYPE: PRT
<213> ORGANISM: Artificial sequence
<220> FEATURE:
<223> OTHER INFORMATION: synthesized HR108
<220> FEATURE:
<221> NAME/KEY: SITE
<222> LOCATION: (14)..(14)
<223> OTHER INFORMATION: Xaa is Nle = norleucine

<400> SEQUENCE: 111

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Cys Cys
        35                  40

```
<210> SEQ ID NO 112
<211> LENGTH: 39
<212> TYPE: PRT
<213> ORGANISM: Artificial sequence
<220> FEATURE:
<223> OTHER INFORMATION: synthesized HR109
<220> FEATURE:
<221> NAME/KEY: SITE
<222> LOCATION: (14)..(14)
<223> OTHER INFORMATION: Xaa is Nle = norleucine

<400> SEQUENCE: 112

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Lys
        35

<210> SEQ ID NO 113
<211> LENGTH: 40
<212> TYPE: PRT
<213> ORGANISM: Artificial sequence
<220> FEATURE:
<223> OTHER INFORMATION: synthesized HR110
<220> FEATURE:
<221> NAME/KEY: SITE
<222> LOCATION: (14)..(14)
<223> OTHER INFORMATION: Xaa is Nle = norleucine

<400> SEQUENCE: 113

His Ala Glu Gly Thr Phe Thr Ser Asp Leu Ser Lys Gln Xaa Glu Glu
1               5                   10                  15

Glu Ala Val Arg Leu Phe Ile Glu Trp Leu Gln Lys Gly Gly Pro Ser
            20                  25                  30

Ser Gly Ala Pro Pro Pro Lys Lys
        35                  40

<210> SEQ ID NO 114
<211> LENGTH: 39
<212> TYPE: PRT
<213> ORGANISM: Artificial sequence
<220> FEATURE:
<223> OTHER INFORMATION: synthesized HR111

<400> SEQUENCE: 114

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Ser
        35

<210> SEQ ID NO 115
<211> LENGTH: 39
<212> TYPE: PRT
<213> ORGANISM: Artificial sequence
<220> FEATURE:
<223> OTHER INFORMATION: synthesized HR112

<400> SEQUENCE: 115

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30
```

Ser Gly Ala Pro Pro Pro Cys
        35

<210> SEQ ID NO 116
<211> LENGTH: 40
<212> TYPE: PRT
<213> ORGANISM: Artificial sequence
<220> FEATURE:
<223> OTHER INFORMATION: synthesized HR113

<400> SEQUENCE: 116

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys Cys
        35                  40

<210> SEQ ID NO 117
<211> LENGTH: 39
<212> TYPE: PRT
<213> ORGANISM: Artificial sequence
<220> FEATURE:
<223> OTHER INFORMATION: synthesized HR114

<400> SEQUENCE: 117

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys
        35

<210> SEQ ID NO 118
<211> LENGTH: 40
<212> TYPE: PRT
<213> ORGANISM: Artificial sequence
<220> FEATURE:
<223> OTHER INFORMATION: synthesized HR115

<400> SEQUENCE: 118

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys Cys
        35                  40

<210> SEQ ID NO 119
<211> LENGTH: 39
<212> TYPE: PRT
<213> ORGANISM: Artificial sequence
<220> FEATURE:
<223> OTHER INFORMATION: synthesized HR116

<400> SEQUENCE: 119

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Lys
        35

```
<210> SEQ ID NO 120
<211> LENGTH: 40
<212> TYPE: PRT
<213> ORGANISM: Artificial sequence
<220> FEATURE:
<223> OTHER INFORMATION: synthesized HR117

<400> SEQUENCE: 120

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Lys Lys
        35                  40

<210> SEQ ID NO 121
<211> LENGTH: 39
<212> TYPE: PRT
<213> ORGANISM: Artificial sequence
<220> FEATURE:
<223> OTHER INFORMATION: synthesized HR118

<400> SEQUENCE: 121

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Ser
        35

<210> SEQ ID NO 122
<211> LENGTH: 39
<212> TYPE: PRT
<213> ORGANISM: Artificial sequence
<220> FEATURE:
<223> OTHER INFORMATION: synthesized HR119

<400> SEQUENCE: 122

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys
        35

<210> SEQ ID NO 123
<211> LENGTH: 40
<212> TYPE: PRT
<213> ORGANISM: Artificial sequence
<220> FEATURE:
<223> OTHER INFORMATION: synthesized HR120

<400> SEQUENCE: 123

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys Cys
        35                  40

<210> SEQ ID NO 124
<211> LENGTH: 39
<212> TYPE: PRT
<213> ORGANISM: Artificial sequence
```

```
<220> FEATURE:
<223> OTHER INFORMATION: synthesized HR121

<400> SEQUENCE: 124

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys
        35

<210> SEQ ID NO 125
<211> LENGTH: 40
<212> TYPE: PRT
<213> ORGANISM: Artificial sequence
<220> FEATURE:
<223> OTHER INFORMATION: synthesized HR122

<400> SEQUENCE: 125

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys Cys
        35                  40

<210> SEQ ID NO 126
<211> LENGTH: 39
<212> TYPE: PRT
<213> ORGANISM: Artificial sequence
<220> FEATURE:
<223> OTHER INFORMATION: synthesized HR123

<400> SEQUENCE: 126

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Lys
        35

<210> SEQ ID NO 127
<211> LENGTH: 40
<212> TYPE: PRT
<213> ORGANISM: Artificial sequence
<220> FEATURE:
<223> OTHER INFORMATION: synthesized HR124

<400> SEQUENCE: 127

His Ala Glu Gly Thr Phe Thr Ser Asp Leu Ser Lys Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Lys Lys
        35                  40

<210> SEQ ID NO 128
<211> LENGTH: 39
<212> TYPE: PRT
<213> ORGANISM: Artificial sequence
<220> FEATURE:
<223> OTHER INFORMATION: synthesized HR125
<220> FEATURE:
<221> NAME/KEY: SITE
```

```
<222> LOCATION: (14)..(14)
<223> OTHER INFORMATION: Xaa is Nle = norleucine

<400> SEQUENCE: 128

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Ser
        35

<210> SEQ ID NO 129
<211> LENGTH: 39
<212> TYPE: PRT
<213> ORGANISM: Artificial sequence
<220> FEATURE:
<223> OTHER INFORMATION: synthesized HR126
<220> FEATURE:
<221> NAME/KEY: SITE
<222> LOCATION: (14)..(14)
<223> OTHER INFORMATION: Xaa is Nle = norleucine

<400> SEQUENCE: 129

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys
        35

<210> SEQ ID NO 130
<211> LENGTH: 40
<212> TYPE: PRT
<213> ORGANISM: Artificial sequence
<220> FEATURE:
<223> OTHER INFORMATION: synthesized HR127
<220> FEATURE:
<221> NAME/KEY: SITE
<222> LOCATION: (14)..(14)
<223> OTHER INFORMATION: Xaa is Nle = norleucine

<400> SEQUENCE: 130

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys Cys
        35                  40

<210> SEQ ID NO 131
<211> LENGTH: 39
<212> TYPE: PRT
<213> ORGANISM: Artificial sequence
<220> FEATURE:
<223> OTHER INFORMATION: synthesized HR128
<220> FEATURE:
<221> NAME/KEY: SITE
<222> LOCATION: (14)..(14)
<223> OTHER INFORMATION: Xaa is Nle = norleucine

<400> SEQUENCE: 131

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30
```

```
Ser Gly Ala Pro Pro Cys
        35
```

```
<210> SEQ ID NO 132
<211> LENGTH: 40
<212> TYPE: PRT
<213> ORGANISM: Artificial sequence
<220> FEATURE:
<223> OTHER INFORMATION: synthesized HR129
<220> FEATURE:
<221> NAME/KEY: SITE
<222> LOCATION: (14)..(14)
<223> OTHER INFORMATION: Xaa is Nle = norleucine

<400> SEQUENCE: 132

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys Cys
        35                  40
```

```
<210> SEQ ID NO 133
<211> LENGTH: 39
<212> TYPE: PRT
<213> ORGANISM: Artificial sequence
<220> FEATURE:
<223> OTHER INFORMATION: synthesized HR130
<220> FEATURE:
<221> NAME/KEY: SITE
<222> LOCATION: (14)..(14)
<223> OTHER INFORMATION: Xaa is Nle = norleucine

<400> SEQUENCE: 133

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Lys
        35
```

```
<210> SEQ ID NO 134
<211> LENGTH: 40
<212> TYPE: PRT
<213> ORGANISM: Artificial sequence
<220> FEATURE:
<223> OTHER INFORMATION: synthesized HR131
<220> FEATURE:
<221> NAME/KEY: SITE
<222> LOCATION: (14)..(14)
<223> OTHER INFORMATION: Xaa is Nle = norleucine

<400> SEQUENCE: 134

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Lys Lys
        35                  40
```

```
<210> SEQ ID NO 135
<211> LENGTH: 39
<212> TYPE: PRT
<213> ORGANISM: Artificial sequence
<220> FEATURE:
<223> OTHER INFORMATION: synthesized HR132
<220> FEATURE:
```

```
<221> NAME/KEY: SITE
<222> LOCATION: (14)..(14)
<223> OTHER INFORMATION: Xaa is Nle = norleucine

<400> SEQUENCE: 135

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Ser
        35

<210> SEQ ID NO 136
<211> LENGTH: 39
<212> TYPE: PRT
<213> ORGANISM: Artificial sequence
<220> FEATURE:
<223> OTHER INFORMATION: synthesized HR133
<220> FEATURE:
<221> NAME/KEY: SITE
<222> LOCATION: (14)..(14)
<223> OTHER INFORMATION: Xaa is Nle = norleucine

<400> SEQUENCE: 136

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys
        35

<210> SEQ ID NO 137
<211> LENGTH: 40
<212> TYPE: PRT
<213> ORGANISM: Artificial sequence
<220> FEATURE:
<223> OTHER INFORMATION: synthesized HR134
<220> FEATURE:
<221> NAME/KEY: SITE
<222> LOCATION: (14)..(14)
<223> OTHER INFORMATION: Xaa is Nle = norleucine

<400> SEQUENCE: 137

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys Cys
        35                  40

<210> SEQ ID NO 138
<211> LENGTH: 39
<212> TYPE: PRT
<213> ORGANISM: Artificial sequence
<220> FEATURE:
<223> OTHER INFORMATION: synthesized HR135
<220> FEATURE:
<221> NAME/KEY: SITE
<222> LOCATION: (14)..(14)
<223> OTHER INFORMATION: Xaa is Nle = norleucine

<400> SEQUENCE: 138

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30
```

```
Ser Gly Ala Pro Pro Cys
        35

<210> SEQ ID NO 139
<211> LENGTH: 40
<212> TYPE: PRT
<213> ORGANISM: Artificial sequence
<220> FEATURE:
<223> OTHER INFORMATION: synthesized HR136
<220> FEATURE:
<221> NAME/KEY: SITE
<222> LOCATION: (14)..(14)
<223> OTHER INFORMATION: Xaa is Nle = norleucine

<400> SEQUENCE: 139

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Cys Cys
        35                  40

<210> SEQ ID NO 140
<211> LENGTH: 39
<212> TYPE: PRT
<213> ORGANISM: Artificial sequence
<220> FEATURE:
<223> OTHER INFORMATION: synthesized HR137
<220> FEATURE:
<221> NAME/KEY: SITE
<222> LOCATION: (14)..(14)
<223> OTHER INFORMATION: Xaa is Nle = norleucine

<400> SEQUENCE: 140

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Lys
        35

<210> SEQ ID NO 141
<211> LENGTH: 40
<212> TYPE: PRT
<213> ORGANISM: Artificial sequence
<220> FEATURE:
<223> OTHER INFORMATION: synthesized HR138
<220> FEATURE:
<221> NAME/KEY: SITE
<222> LOCATION: (14)..(14)
<223> OTHER INFORMATION: Xaa is Nle = norleucine

<400> SEQUENCE: 141

His Ala Glu Gly Thr Phe Thr Ser Asp Leu Ser Lys Gln Xaa Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Lys Lys
        35                  40
```